United States Patent [19]
Nakamura et al.

[11] Patent Number: 5,001,556
[45] Date of Patent: Mar. 19, 1991

[54] ENDOSCOPE APPARATUS FOR PROCESSING A PICTURE IMAGE OF AN OBJECT BASED ON A SELECTED WAVELENGTH RANGE

[75] Inventors: Kazunari Nakamura; Yutaka Takahashi, both of Hachioji, Japan

[73] Assignee: Olympus Optical Co., Ltd., Tokyo, Japan

[21] Appl. No.: 497,826

[22] Filed: Mar. 22, 1990

Related U.S. Application Data

[63] Continuation of Ser. No. 247,187, Sep. 21, 1988, abandoned.

[30] Foreign Application Priority Data

| Sep. 30, 1987 | [JP] | Japan | 62-247284 |
| Oct. 20, 1987 | [JP] | Japan | 62-266060 |
| Feb. 8, 1988 | [JP] | Japan | 62-26838 |
| Apr. 28, 1988 | [JP] | Japan | 62-105971 |

[51] Int. Cl.$^5$ .................... H04N 7/18; A61B 1/06
[52] U.S. Cl. .................... 358/98; 358/213.19; 128/6
[58] Field of Search .............. 358/38, 213.19; 128/4, 128/6

[56] References Cited

U.S. PATENT DOCUMENTS

| 4,618,884 | 10/1986 | Nagasaki | 358/98 |
| 4,621,284 | 11/1986 | Nishioka et al. | 358/98 |
| 4,622,584 | 11/1986 | Nagasaki et al. | 358/98 |
| 4,625,236 | 11/1986 | Fujimori et al. | 358/98 |
| 4,653,478 | 3/1987 | Nagasaki et al. | 358/98 |
| 4,656,508 | 4/1987 | Yokata | 358/98 |
| 4,685,451 | 8/1987 | Ando | 128/6 |
| 4,689,687 | 8/1987 | Koike et al. | 358/213.2 X |
| 4,729,018 | 3/1988 | Watanabe et al. | 358/98 |
| 4,783,702 | 11/1988 | Sone et al. | 358/213.19 |
| 4,807,026 | 2/1989 | Nishioka et al. | 358/98 |

Primary Examiner—John K. Peng
Attorney, Agent, or Firm—Armstrong, Nikaido, Marmelstein, Kubovcik & Murray

[57] ABSTRACT

An endoscope apparatus whereby the observing wavelength range can be selected in response to an object to be observed has a light source part emitting a light illuminating the object. An endoscope body has an elongated insertable part having an observing window and illuminating window in the tip part, a light transmitter transmitting the light of the light source part and emitting the light to the object from the illuminating window and an image forming optical system receiving the returning light from the object entering through the observing window and forming an object image. The object image formed by the image forming optical system is imaged on a solid state imaging device. An electric signal is output from the solid state imaging device and is processed by a signal processing circuit and a picture image is displayed. The object image is separated into a plurality of wavelength ranges by wavelength range separating filters. A selecting apparatus selects a picture image based on the wavelength range clearly representing the state of the object from among the picture images obtained by a plurality of separated wavelength ranges.

35 Claims, 24 Drawing Sheets

FIG.10
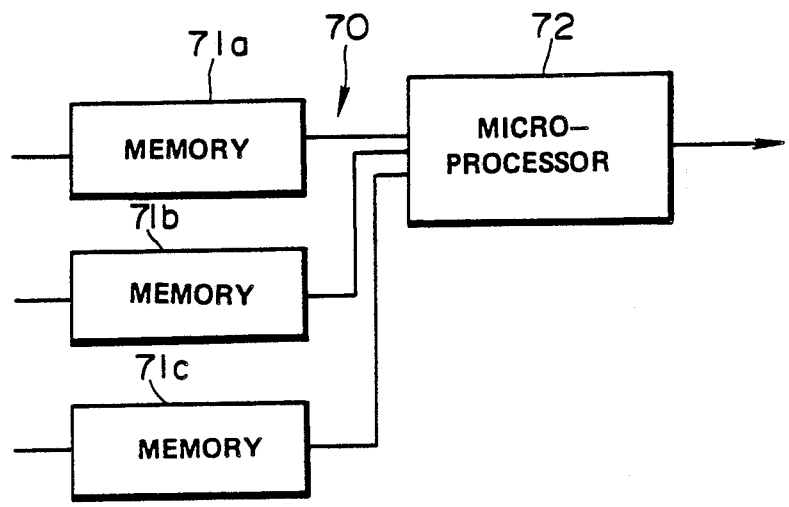
FIG.12
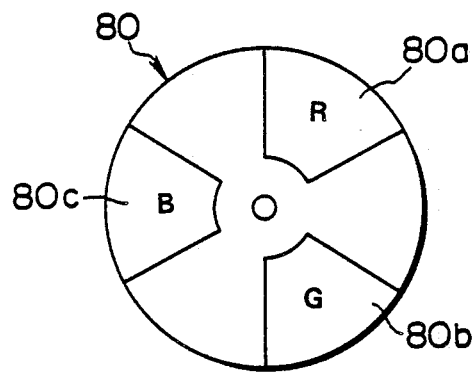
FIG.13
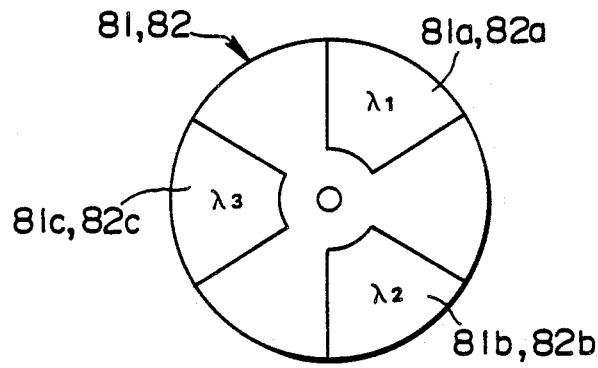
FIG.15

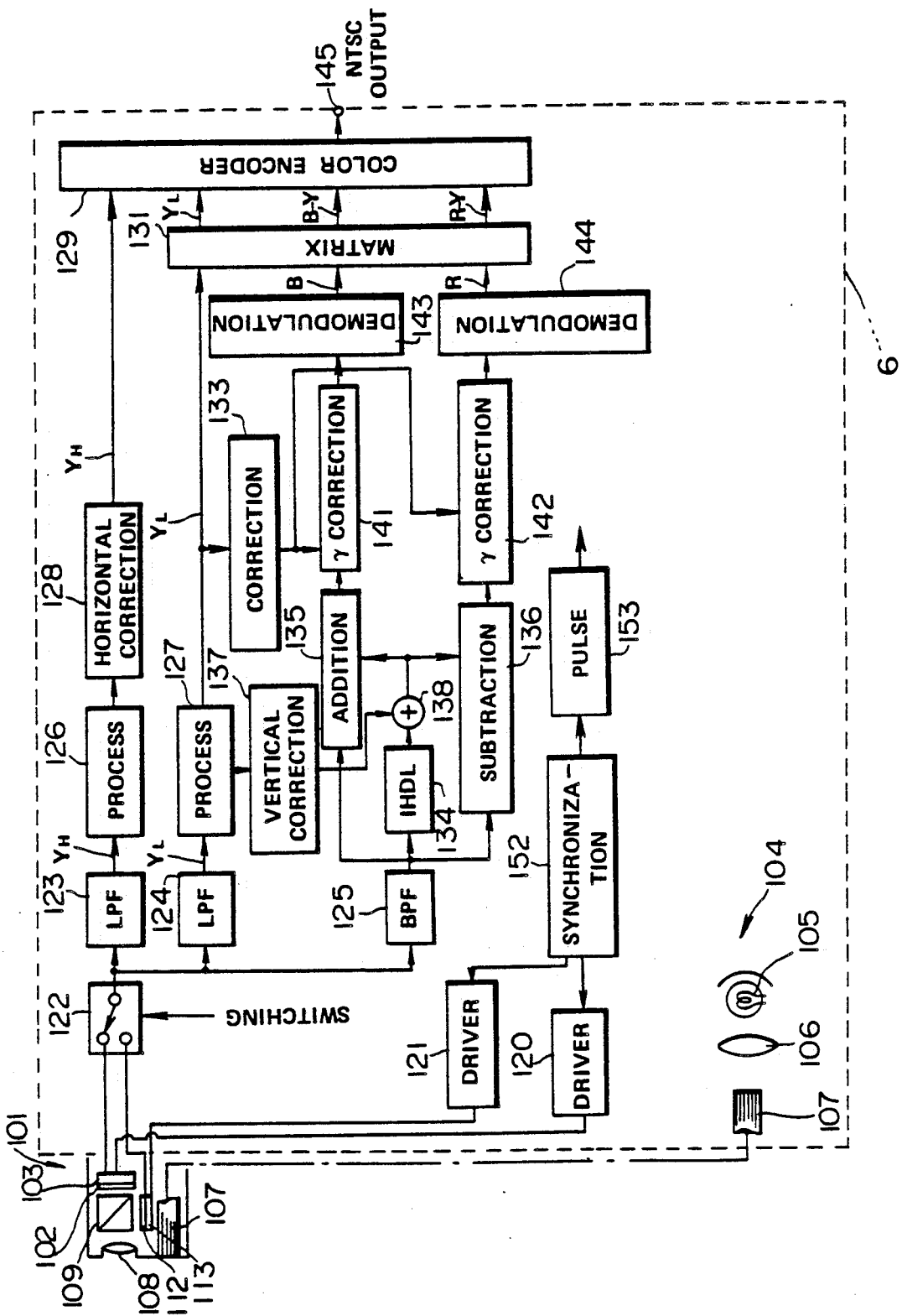

▨ SIGNAL CHARGE   ▦ UNNECESSARY CHARGE

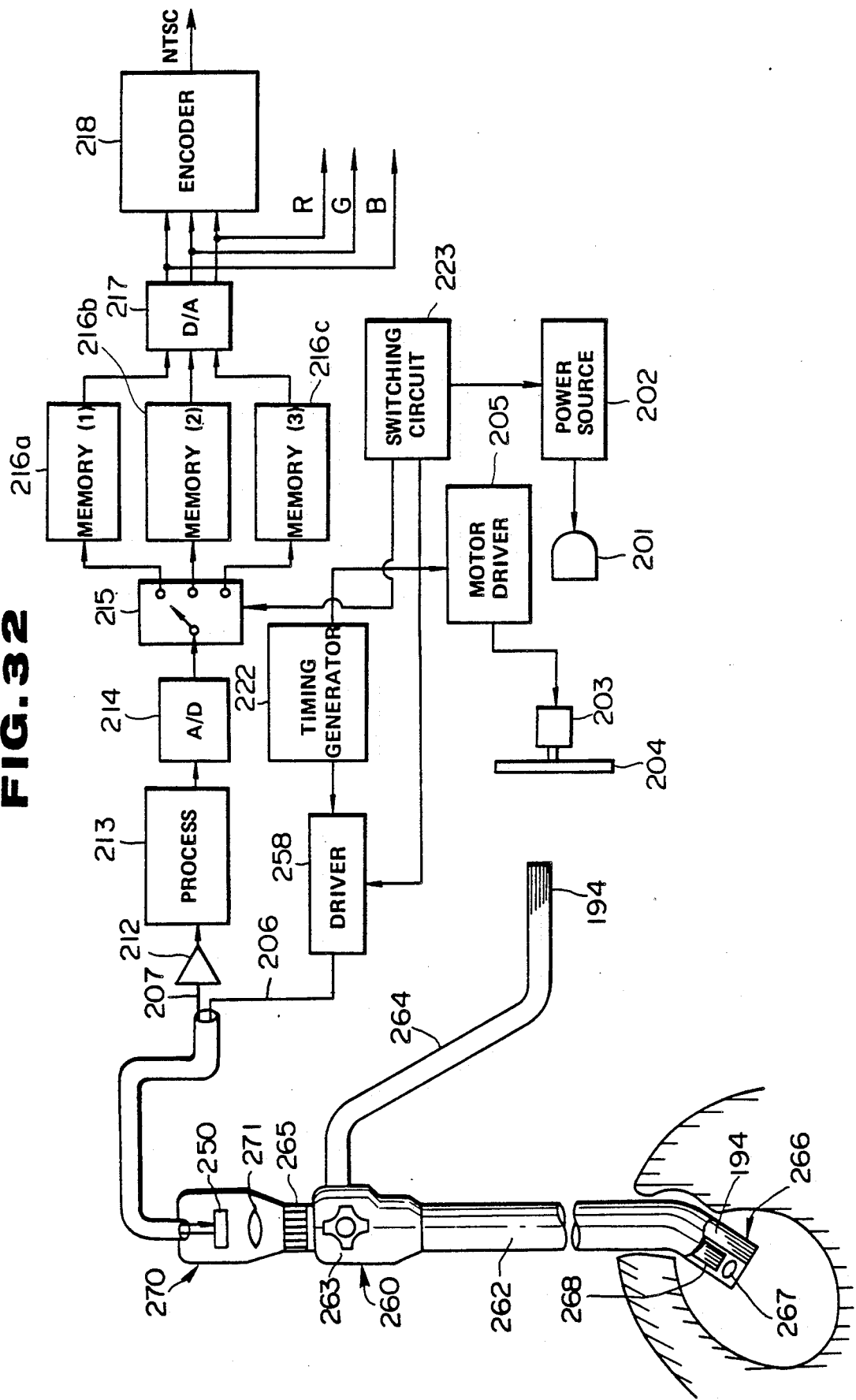

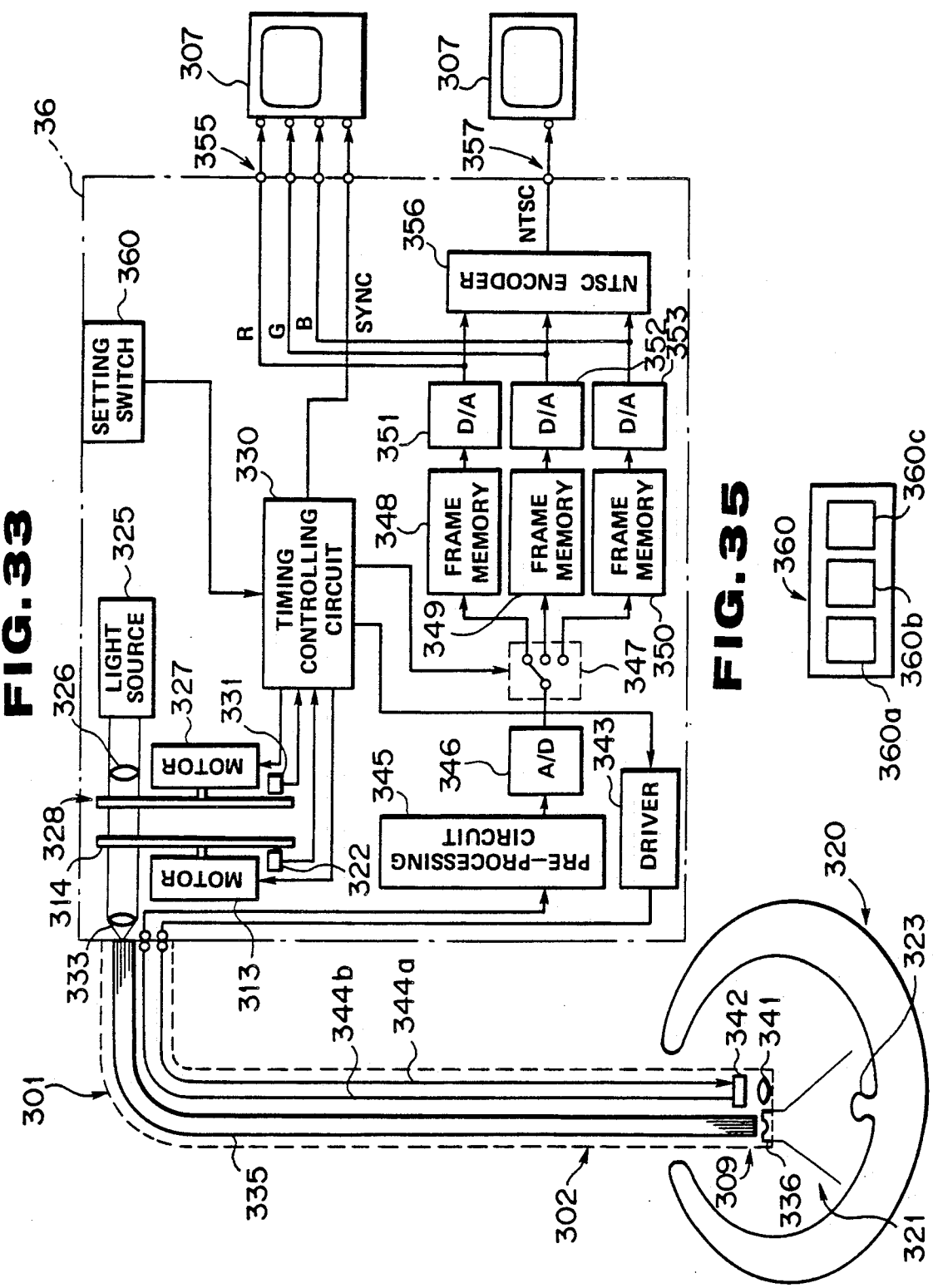

ENDOSCOPE APPARATUS FOR PROCESSING A PICTURE IMAGE OF AN OBJECT BASED ON A SELECTED WAVELENGTH RANGE

This application is a continuation of application Ser. No. 247,187, filed Sept. 21, 1988, now abandoned.

FIELD OF THE INVENTION

This invention relates to an endoscope apparatus whereby the observing wavelength range can be selected in response to the observed object.

BACKGROUND OF THE INVENTION

Recently, an electronic endoscope wherein such solid state imaging device as a charge coupled device (CCD) is used as an imaging means is variously suggested.

Such electronic endoscope has advantages as compared with a fiber scope that the resolution is higher, it is easier to record and reproduce picture images and such picture image processing as the magnification and comparison of picture images is easier.

Now, in the case of observing an object by using such imaging apparatus as the above mentioned electronic endoscope, particularly, in the case of distinguishing the affected part and normal part from each other within a living body, it will be necessary to sense (recognize) a delicate tone difference. However, in case the variation of the tone in the observed part is delicate, a high knowledge and experience will be required to sense .this delicate difference. Further, a long time will be required until it is sensed. Even if attentions are concentrated during the sensing, it has been difficult to always make a proper judgment.

In order to cope with such circumstances, for example, in the publication of a Japanese patent application laid open No. 3033/1981, by noting that, in such other range than the visible range as, for example, an infrared wavelength range, some variation of the tone may be large, there is disclosed a technique wherein a spectral light having at least one infrared wavelength range is led in time series to illuminate an object to be observed, the reflected light from the observed object is made to form an image on a solid state imaging device and is converted to a electric signal and the electric signal is processed in response to the wavelength range to display a picture image in the wavelength range with a specific color signal. According to this prior art example, the invisible information obtained in the infrared wavelength range can be converted to a visible information and, for example, the affected part and normal part can be quickly and easily discriminated from each other.

On the other hand, it is known to be useful for the early discovery or the like of a disease to know the amount of hemoglobin and the distribution of the oxygen saturation degree in a blood. As a method of determining the amount of hemoglobin and the oxygen saturation degree in the blood, for example, as shown in the publication of a Japanese utility model application laid open No. 151705/1986, there is a method of determining them from picture images in a plurality of specific wavelength ranges.

However, in the above mentioned prior art example, the combination of illuminating lights, that is, the observing wavelength is fixed (by the combination, for example, of green, blue and infrared if they are used) and the combination of illuminating lights could not be simply varied. That is to say, in the case of observing by varying the combination of illuminating lights, the rotary filter will have to be replaced each time. Further, the combination of green, blue and infrared will not be always effective to all the disease parts. That is to say, it is well considered that, in some affected part, as compared with the stomach wall, the absorption coefficient in the wavelength range on the side of the wavelength longer than of the red light or in the short wavelength range is greatly different.

The medical study of the special light observation has not yet been well made but will be positively made hereafter. It is strongly required that the disease part should be observed by varying the combination of illuminating lights and what combination of illuminating lights is effective to the discrimination from the peripheral side part depending on the kind of the disease part should be investigated and should be applied to the diagnosis on the basis of the results.

OBJECT AND SUMMARY OF THE INVENTION

An object of the present invention is to provide an endoscope apparatus whereby a picture image information can be obtained by selecting the wavelength range clearly representing the state of an observed object and the respective parts of the observed object difficult to discriminate with a picture image in the general visible range can be easily observed.

The endoscope apparatus of the present invention comprises a light source part emitting a light illuminating an object to be imaged; an endoscope body having an elongated insertable part having an observing window and illuminating window in the tip part, a light transmitter transmitting the light of the above mentioned light source part and emitting the light to the object from the above mentioned illuminating window and an image forming optical system receiving the returning light from the object entering through the above mentioned observing window and forming an object image; an imaging means imaging the object image formed by the above mentioned image forming optical system and outputting it as an electric signal; a signal processing means processing the electric signal of the above mentioned imaging means and displaying a picture image; a wavelength range separating means separating the above mentioned object image into a plurality of wavelength ranges; and a selecting means selecting the picture image based on the wavelength range clearly representing the state of the object from among the picture images obtained by a plurality of the above mentioned separated wavelength ranges.

The other features and advantages of the present invention will become apparent enough from the following explanation.

BRIEF DESCRIPTION OF THE DRAWINGS

FIGS. 1 to 10 relate to the first embodiment of the present invention.

FIG. 1 is a block diagram showing the formation of an endoscope apparatus.

FIG. 2 is an explanatory view showing a rotary filter.

FIG. 3 is a side view showing an entire endoscope.

FIG. 4 is an explanatory diagram showing the variation of a light absorbing degree of a blood with the variation of an oxygen saturation degree of hemoglobin.

FIG. 5 is an explanatory diagram showing transmitted wavelength ranges of respective filters for special picture images of a rotary filter.

FIG. 6 is an explanatory diagram showing another example of transmitted wavelength ranges of respective filters for special picture images of a rotary filter.

FIG. 7 is an explanatory diagram showing spectral transmitting characteristics of respective filters for the ordinary observation of a rotary filter.

FIG. 8 is an explanatory diagram showing spectral transmitting characteristics of respective filters for special picture images of a rotary filter.

FIG. 9 is a block diagram showing processing circuits for determining the amount of hemoglobin and the oxygen saturation degree.

FIG. 10 is a block diagram showing another example of processing circuits for determining the amount of hemoglobin and the oxygen saturation degree.

FIGS. 11 to 13 relate to the second embodiment of the present invention.

FIG. 11 is a block diagram showing the formation of an endoscope.

FIG. 12 is an explanatory view showing a rotary filter for the ordinary observation.

FIG. 13 is an explanatory view showing a rotary filter for special picture images.

FIGS. 14 and 15 relate to the third embodiment of the present invention.

FIG. 14 is a block diagram showing the formation of an endoscope apparatus.

FIG. 15 is an explanatory view showing a color filter array.

FIG. 16 is a block diagram showing the formation of an endoscope.

FIG. 17 is an explanatory view showing a rotary filter.

FIG. 19 is a block diagram showing the formation of an imaging apparatus.

FIG. 20 is an explanatory view showing a rotary filter.

FIG. 21 is an explanatory diagram showing the transmitting characteristics of respective filters of a rotary filter.

FIG. 22 is an explanatory diagram showing absorption spectra of respective colors of a living body.

FIG. 23 is an explanatory view of a shutter ass arranged between a lamp and rotary filter.

FIG. 24 is an explanatory view of a shutter as arranged between a rotary filter and light guide.

FIG. 25 is an explanatory view of a shutter as provided on the exit end surface of a light guide.

FIG. 26 is an explanatory view showing the formation of a CCD.

FIGS. 27a and 27b are explanatory views showing a shutter.

FIGS. 28 to 31 relate to the eighth embodiment of the present invention.

FIG. 28 is a block diagram showing the formation of an imaging apparatus.

FIG. 29 is an explanatory view showing the formation of a CCD fitted with an electronic shutter.

FIGS. 30a–30c are an explanatory view showing the operation of an electronic shutter.

FIGS. 31a–31c are a timing chart showing the operation of this embodiment.

FIG. 32 is an explanatory view showing the formation of an endoscope apparatus relating to the ninth embodiment of the present invention.

FIGS. 33 to 38 relate to the tenth embodiment of the present invention.

FIG. 33 is a block diagram showing the formation of an electronic endoscope apparatus.

FIGS. 34a–34f is a timing chart view for explaining the operations of an illuminating light and CCD reading-out.

FIG. 35 is an explanatory view showing a setting switch.

FIG. 36 is an explanatory diagram showing spectral transmittivities of respective filters of a rotary filter.

FIG. 37 is an explanatory view of a light intercepting plate.

FIG. 38 is an explanatory view of a rotary filter.

DETAILED DESCRIPTION OF THE PREFERRED EMBODIMENTS

FIGS. 1 to 10 show the first embodiment of the present invention.

Figure 3:
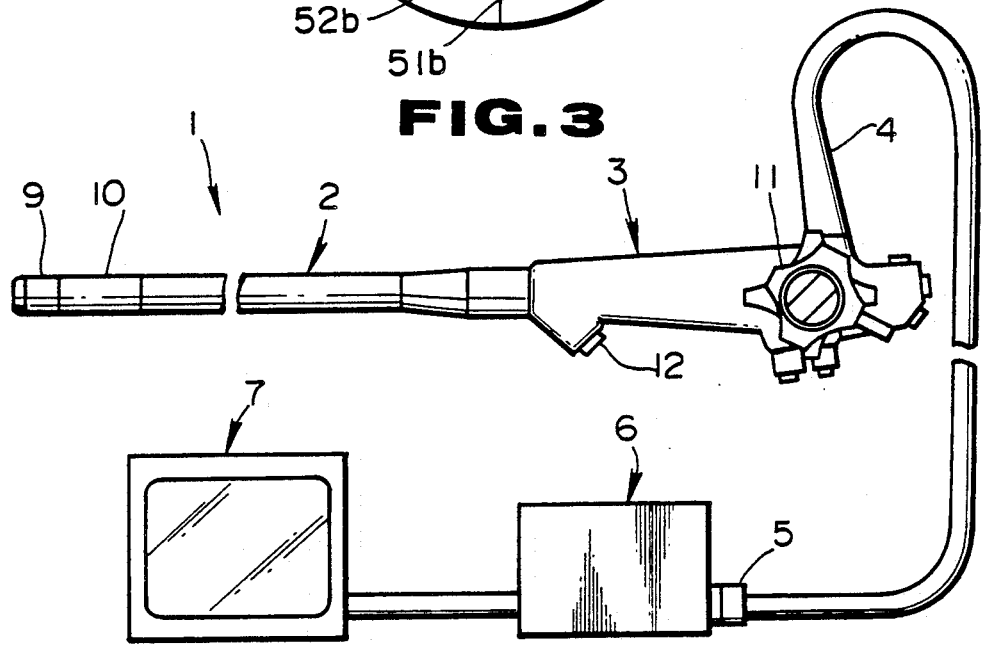

As shown in FIG. 3, the endoscope apparatus of this embodiment is provided with an electronic endoscope 1 which has an elongated, for example, flexible insertable part 2 and a thick operating part 3 provided at the rear-end of this insertable part 2. A flexible cable 4 is extended sidewise from the rear end part of the above mentioned operating part 3 and is provided at the tip with a connector 5 so that the above mentioned electronic endoscope 1 may be connected through the above mentioned connector 5 to a video processor 6 containing a light source apparatus and signal processing circuit. Further, a monitor 7 is to be connected to the above mentioned video processor 6.

The above mentioned insertable part 2 is provided on the tip side in turn with a rigid tip part 9 and a rearward curvable part 10 adjacent to this tip part 9. The above mentioned curvable part 10 can be curved horizontally and vertically by rotating a curving knob 11 provided on the above mentioned operating part. The above mentioned operating part 3 is provided with an inserting part 12 communicating with a treating tool channel provided within the above mentioned insertable part 2.

Figure 1:
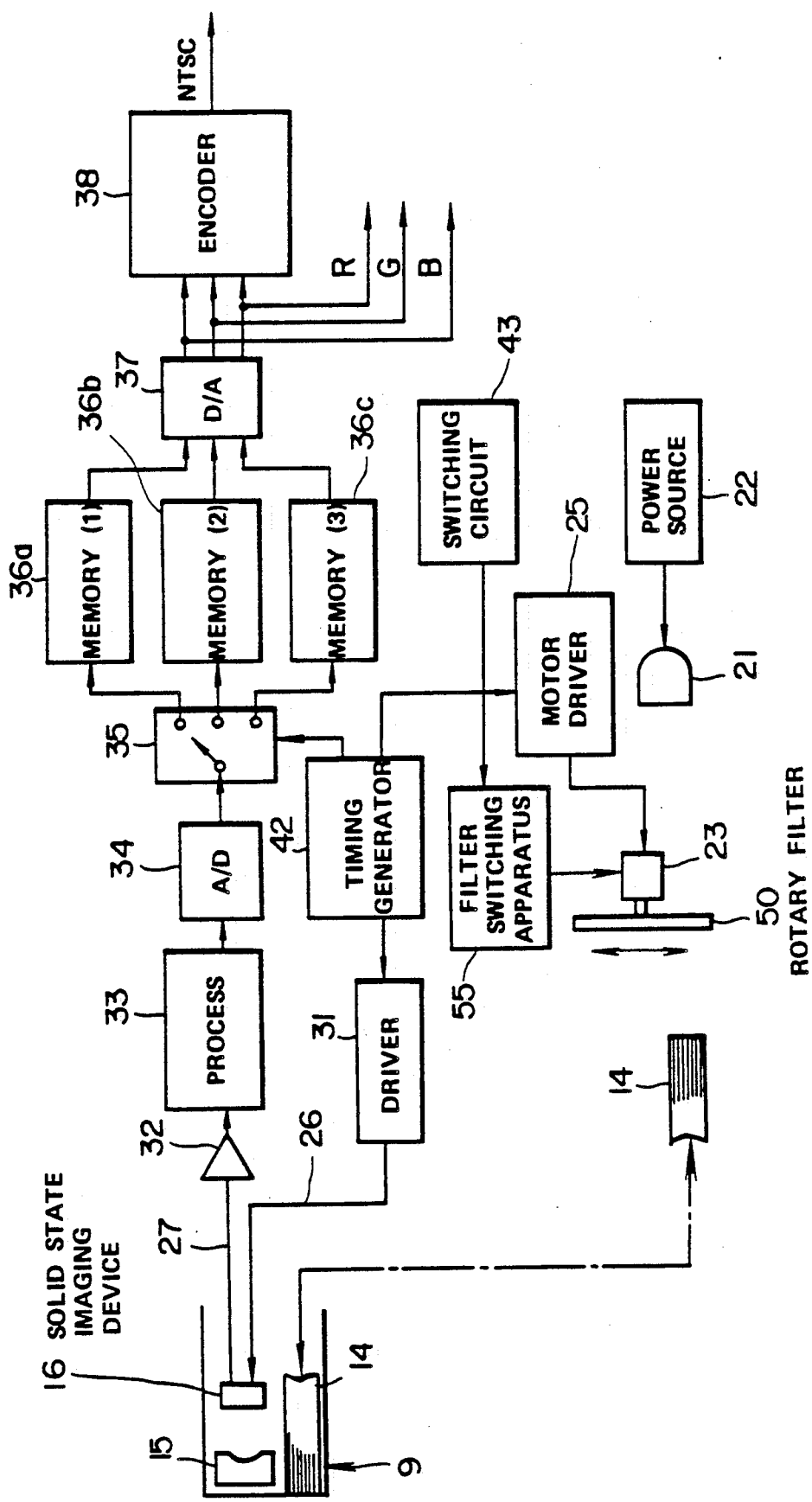

As shown in FIG. 1, a light guide 14 transmitting an illuminating light is inserted through the insertable part 2 of the electronic endoscope 1. This light guide 14 is arranged on the tip surface in the tip part 9 of the insertable part 2 so that the illuminating light may be emitted from this tip part 9. The above mentioned light guide 14 is inserted on the entrance end side through the universal cord 4 and is connected to the connector 5. The above mentioned tip part 9 is provided with an objective lens system 15 and a solid state imaging device 16 is arranged in the image forming position of this objective lens system 15. This solid state imaging device 16 has a sensitivity in a wide wavelength range from an ultraviolet range to an infrared range including a visible range. Signal lines 26 and 27 are connected to the above mentioned solid state imaging device 16, are inserted through the above mentioned insertable part 2 and universal cord 4 and are connected to the above mentioned connector 5.

Figure 2:
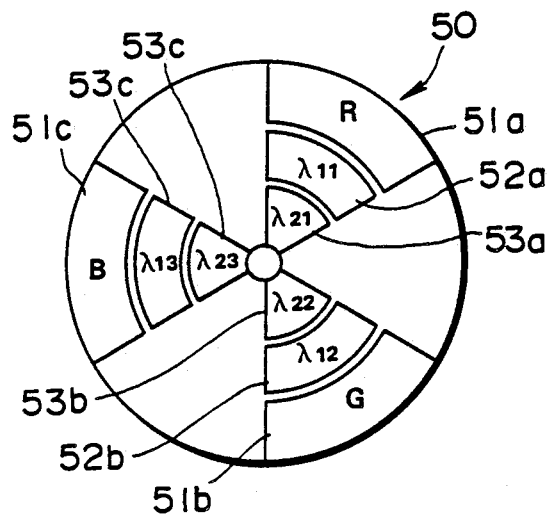

On the other hand, a lamp 21 emitting lights in a wide band from an ultraviolet light to an infrared light is provided within the video processor 6. A general xenon lamp or strobo-lamp can be used for this lamp 21. The above mentioned xenon lamp or strobo-lamp emits large amounts of not only a visible light but also an ultraviolet light and infrared light. This lamp 21 is fed with an electric power by a power source part 22. A rotary filter 50 rotated and driven by a motor 23 is arranged forward of the above mentioned lamp 21 and has three concentrically sectioned parts as shown in FIG. 2. In the outermost peripheral part, filters 51a, 51b and 51c transmitting respectively the lights in the wavelength ranges of red (R), green (G) and blue (B) for the ordinary observation are arranged in the peripheral direction. In the middle part, filters 52a, 52b and 52c transmitting respectively the lights in the narrow bands with wavelengths $\lambda 11$, $\lambda 12$ and $\lambda 13$ as centers for special picture images are arranged in the peripheral direction. In the innermost peripheral part, filters 53a, 53b and 53c transmitting respectively the narrow bands with wavelengths $\lambda 21$, $\lambda 22$ and $\lambda 23$ as centers for special picture images are arranged in the peripheral direction.

Figure 5:
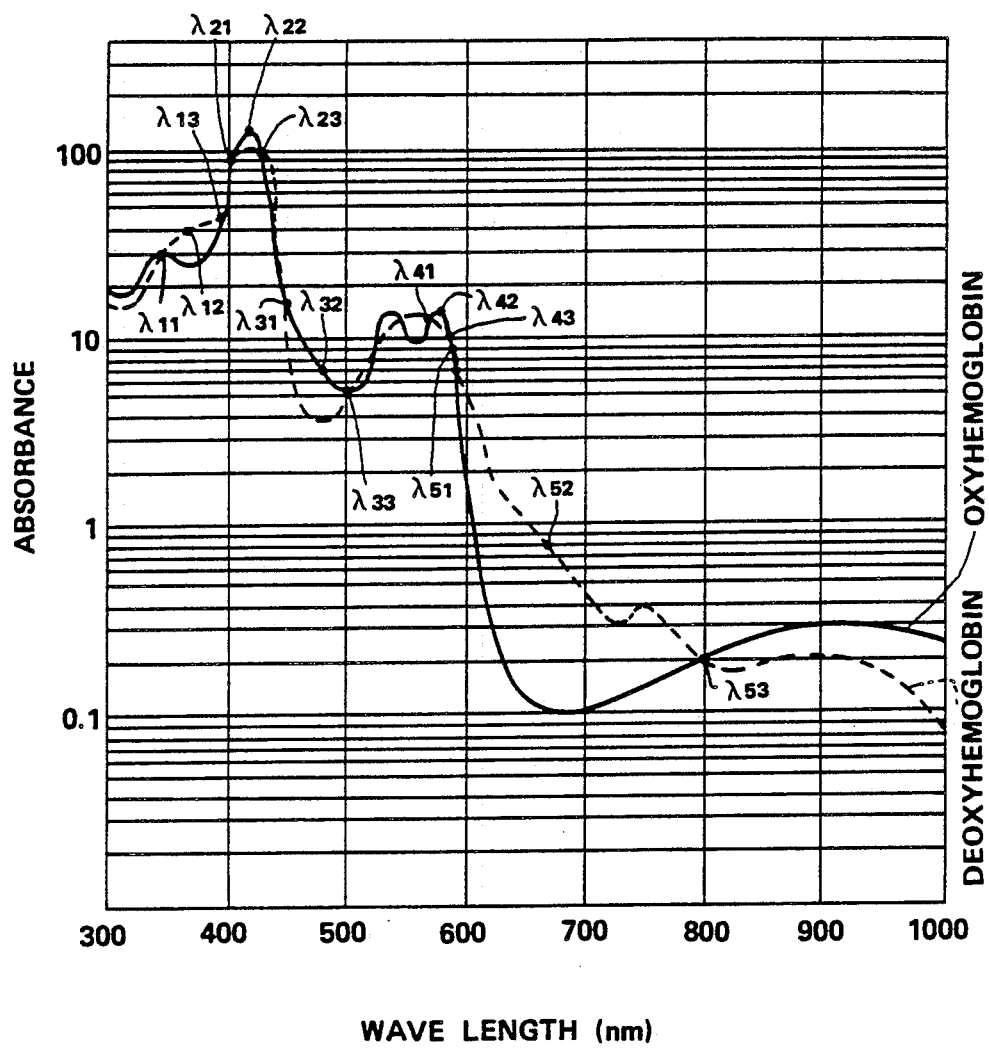
Figure 7:
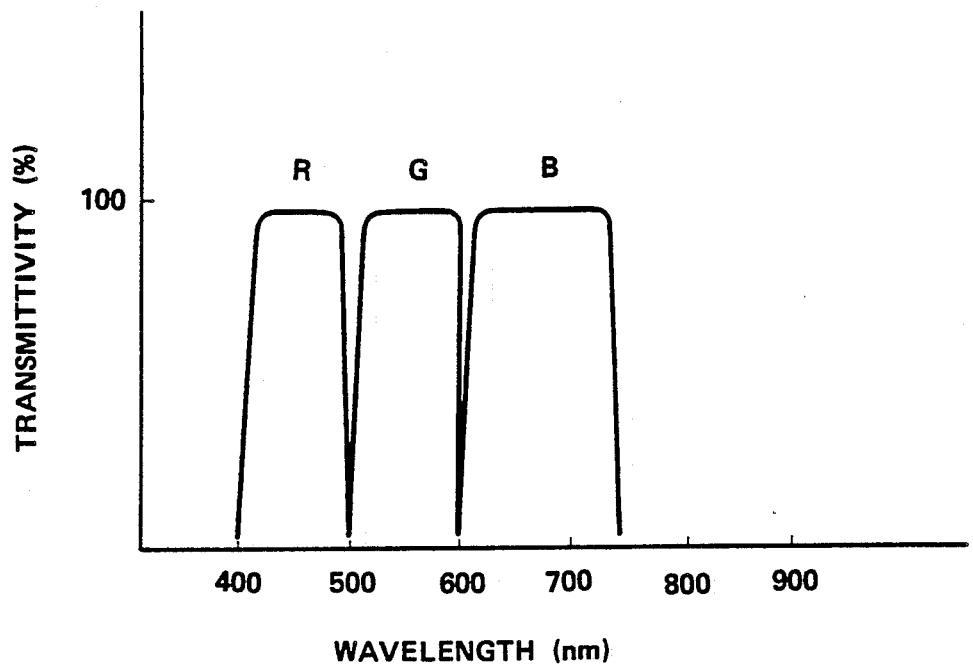
Figure 8:
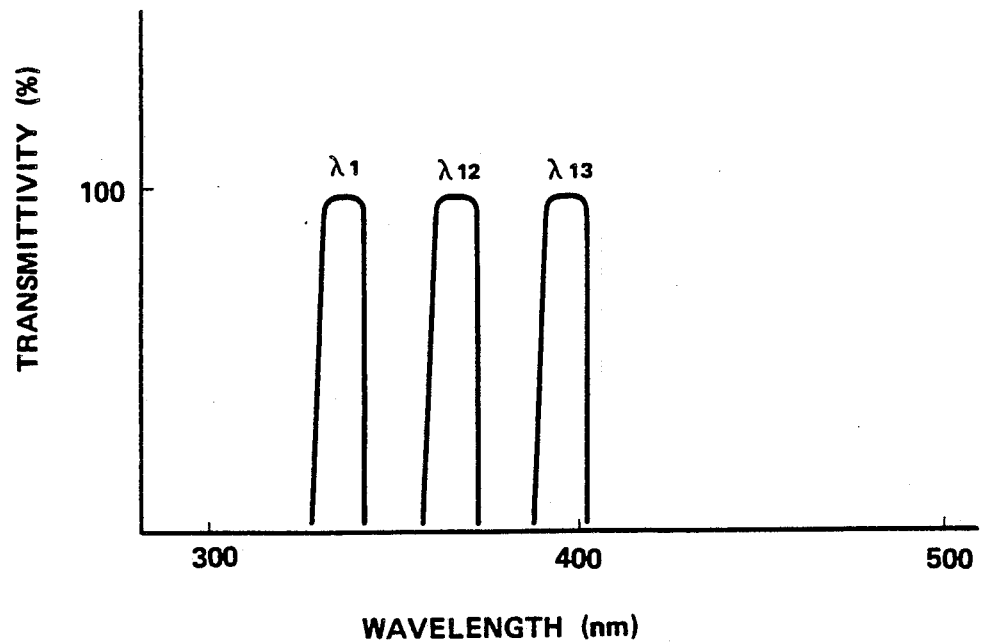

By the way, the transmitting characteristics of the above mentioned filters 51a, 51b and 51c are shown in FIG. 7. On the other hand, the above mentioned wavelengths $\lambda 11$, $\lambda 12$, and $\lambda 13$ and wave lengths $\lambda 21$, $\lambda 22$ and $\lambda 23$ are set as shown in FIG. 5. That is to say, the wavelength group of a set of $\lambda 11$, $\lambda 12$ and $\lambda 13$ for special picture images is a combination of such wavelength at which the light absorbing degree of a blood varies with the variation of the oxygen saturation degree (also mentioned as $SO_2$) of hemoglobin as, for example, $\lambda 12$ and such wavelengths which are near the above mentioned wavelength and at which the light absorbing degree of the blood varies little with the variation of $SO_2$ as, for example, $\lambda 11$ and $\lambda 13$.

By the way, in FIG. 5, the spectral light absorbing characteristics of oxy (oxidized) hemoglobin and deoxy (deoxidized) hemoglobin are shown to show the variation of the light absorbing degree of the blood with the variation of $SO_2$.

Figure 4:
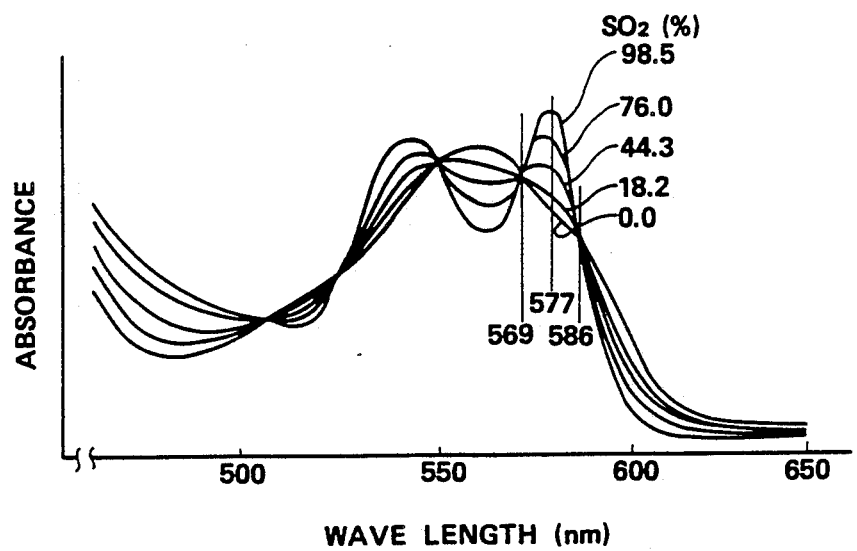

Also, the variation of the light absorbing degree (scattered reflection spectrum) with the variation of $SO_2$ near 500 to 600 m nm. is shown in FIG. 4. As shown in FIG. 4, for example, a set of 569 nm., 577 nm. and 586 nm. is selected as a wavelength group for special picture images in this band.

As shown in FIG. 5, in 300 to 1000 nm., not only the above mentioned $\lambda 11$, $\lambda 12$ and $\lambda 13$ in 300 to 400 nm. and the above mentioned $\lambda 21$, $\lambda 22$ and $\lambda 23$ near 400 nm. but also $\lambda 31$, $\lambda 32$ and $\lambda 33$ in 400 to 500 nm., $\lambda 41$, $\lambda 42$ and $\lambda 43$ in 500 to 600 nm. and $\lambda 51$, $\lambda 52$ and $\lambda 53$ in 450 to 850 nm. can be set as wavelength groups for special picture images. Not only the above mentioned $\lambda 11$, $\lambda 12$ and $\lambda 13$ and $\lambda 21$, $\lambda 22$ and $\lambda 23$ but also any wavelength groups among, for example, the above described five wavelength groups can be selected as transmitted wavelengths of the filters 52a, 52b and 52c and 53a, 53b and 53c in the ranges of the middle part and innermost peripheral part of the above mentioned rotary filter.

The above mentioned motor 23 is controlled in the rotation and driven by a motor driver 25.

A filter switching apparatus 55 controlled by a control signal from a switching circuit 43 is provided in this embodiment. In this filter switching apparatus 55, by varying the positions of the above mentioned rotary filter 50 and motor 23 with respect to the optical axis of the illuminating light path between the lamp 21 and the entrance end of the light guide 14, any of the outermost peripheral part, middle part and innermost peripheral part is selectively interposed in the above mentioned illuminating light path.

The light having passed through the above mentioned rotary filter 50 and separated in time series into lights of the respective wavelength ranges within the selected wavelength group will be made to enter the above mentioned light guide 14 at the entrance end, will be led to the tip part 9 through this light guide 14 and will be emitted from this tip part 9 to illuminate a part to be observed.

The returning light from the observed part by this illuminating light will be made to form an image on the solid state imaging device 16 by the objective lens system 15 and will be photoelectrically converted. A driving pulse from a driver circuit 31 within the above mentioned video processor 6 will be applied to this solid state imaging device 16 through the above mentioned signal line 26 and the reading-out and transfer will be made by this driving pulse. The video signal read out of this solid state imaging device 16 will be input into a pre-amplifier 32 provided within the above mentioned video processor or electronic endoscope 1 through the above mentioned signal line 27. The video signal amplified by this pre-amplifier 32 will be input into a processing circuit 33, will be processed to correct $\gamma$ and balance white and will be converted to a digital signal by an A/D converter 34. This digital video signal will be selectively memorized in three memories (1) 36a, (2) 36b and (3) 36c corresponding to the respective colors, for example, of red (R), green (G) and blue (B) by a selecting circuit 35. The signals will be simultaneously read out of the above mentioned memories (1) 36a, (2) 36b and (3) 36c, will be converted to analog signals by a D/A converter 37 and will be output as R, G and B color signals and will be at the same time input into an encoder 3 and will be output as an NTSC composite signal out of this encoder 38.

The above mentioned R, G and B color signals or NTSC composite signal will be input into the color monitor 7 and the observed part will be color-displayed by this color monitor 7.

A timing generator 42 making a timing of the entire system is provided within the above mentioned video processor 6. Such respective circuits as the motor driver circuit 25, driver circuit 31 and selecting circuit 35 will be synchronized with one another by this timing generator 42.

In this embodiment, when the outermost peripheral part of the rotary filter 50 is interposed in the illuminating light path by controlling a filter switching apparatus 55 with a switching circuit 43, the light emitted from the above mentioned lamp 21 will pass sequentially through the filter 51a, 51b and 51c transmitting respectively R, G and B of the above mentioned rotary filter and will be divided in time series into lights of respective wavelength ranges of R, G and B. These lights of R, G and B will be transmitted to the tip part 9 through the light guide 14 and will be radiated to an object to be imaged. The returning lights from the object by the sequential illuminating lights of R, G and B in the visible band will be made to form an image on the solid state imaging device 16 by the objective lens system 15 and the object image will be imaged by this solid state imaging device 16. Therefore, an ordinary visible picture image will be color-displayed in the monitor 7.

On the other hand, when the middle part or innermost peripheral part of the rotary filter 50 is interposed in the illuminating light path by controlling the filter switching apparatus 55 with the above mentioned switching circuit 43, the light emitted from the above mentioned lamp 21 will pass sequentially through filters 52a, 52b and 52c or 53a, 53b and 53c transmitting respectively a wavelength group of $\lambda 11$, $\lambda 12$ and $\lambda 13$ or of 53c, 53b and 53c of the above mentioned rotary filter 50 and will be divided in time series into lights of respective wavelength ranges within the above mentioned wavelength group. These lights will be transmitted to the tip part 9 through the light guides 14 and will be radiated to an object to be imaged. The returning lights from the object by these illuminating lights will be made to form an image on the solid state imaging device 16 by the objective lens system 15 and the object image will be imaged by this solid state imaging device 1. Therefore, a picture image by a wavelength group of $\lambda 11$, $\lambda 12$ and $\lambda 13$ or $\lambda 21$, $\lambda 22$ and $\lambda 23$ will be displayed in quasi colors in the monitor 7. The variations of the $SO_2$ and hemoglobin amount can be observed with this picture image.

By the way, a picture image by one or two wavelength ranges in the above mentioned wavelength group can be obtained by selectively reading out one or two of the memories 36a, 36b and 36c.

Figure 9:
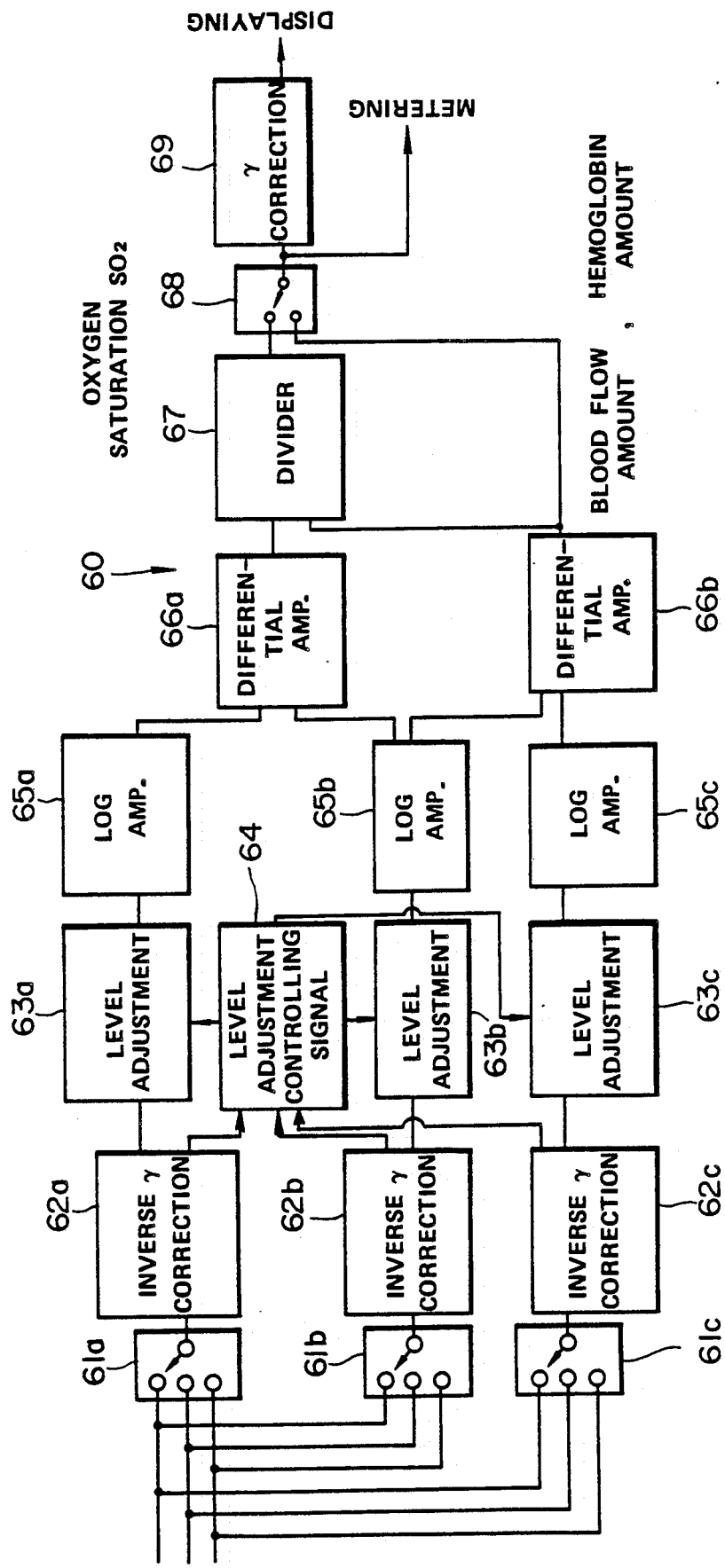

When a special picture image is selected, a picture image showing the $SO_2$ and hemoglobin amount will be able to be obtained by processing the R, G and B signals from the above mentioned video processor 6 with such signal processing circuit 60 as is shown in FIG. 9.

Such respective wavelengths as $\lambda 1$, $\lambda 2$ and $\lambda 3$ in the selected wavelength group shall be explained with reference to the above mentioned signal processing circuit 60. By the way, the above mentioned wavelengths $\lambda 1$ and $\lambda 3$ are wavelengths in which the light absorbing degree will not vary. At all with $SO_2$ and the wavelength $\lambda 2$ is a wavelength in which the light absorbing degree will greatly vary with $SO_2$.

The above mentioned signal processing circuit 60 has three selectors of three inputs and one output each so that picture image signals corresponding to the respective wavelengths in the selected wavelengths group may be applied respectively to the respective input ends of the respective selectors. Also, the above mentioned respective selectors will select and output picture image signals corresponding to wavelengths different from each other. For example, the selector 61a will output a picture image signal corresponding to the wavelength $\lambda 1$, the selector 61b will output a picture image signal corresponding to the wavelength $\lambda 2$ and the selector 61c will output a picture image signal corresponding to the wavelength $\lambda 3$. The outputs of the above mentioned respective selectors 61a, 61b and 61c will be input respectively into inverse $\gamma$ correcting circuits 62a, 62b and 62c and will have $\gamma$ inversely corrected to return to the original state the $\gamma$ correction already made in the above mentioned video processor 6. The outputs of the above mentioned inverse $\gamma$ correcting circuits will be input respectively into level adjusting circuits 63a, 63b and 63c. In these level adjusting circuits, levels will be adjusted by level adjustment controlling signals from a level adjustment controlling signal generating circuit 64. All the levels will be adjusted by the three level adjusting circuits 63a, 63b and 63c. Further, as the ordinate is a logarithmic axis in such diagram showing the variation of the light absorbing degree of the blood with the variation of the oxygen saturation degree as, for example, in FIG. 5, the outputs of the above mentioned level adjusting circuits will be logarithmically converted respectively by logarithmic amplifiers 65a, 65b and 65c.

The outputs of two logarithmic amplifiers 65a and 65b of the three logarithmic amplifiers will be input into a differential amplifier 66a and the difference between the picture image signal corresponding to the wavelength $\lambda 1$ and the picture image signal corresponding to the wavelength $\lambda 2$ will be operated. Likewise, the outputs of two logarithmic amplifiers 65b and 65c will be input into a differential amplifier 66b and the difference between the picture image signal corresponding to the wavelength $\lambda 2$ and the picture image signal corresponding to the wavelength $\lambda 3$ will be operated. Thus, how much oxygen is dissolved in the inspected object, that is, the oxygen saturation degree can be known from the difference between the picture image signals corresponding to the two wavelengths.

The outputs of the above mentioned differential amplifiers 66a and 66b will be used to determine the oxygen saturation degree and will be input into a divider 67. By making a predetermined operation with this divider 67, the above mentioned $SO_2$ will be determined. The output of the above mentioned differential amplifier 66b will be used to determine the blood flow amount and hemoglobin amount. The output of the above mentioned divider 67 and the output of the differential amplifier 66b will be input into a selector 68 of two inputs. One of a signal showing $SO_2$ and a signal showing a blood flow amount and hemoglobin amount will be selectively output out of this selector 68.

The output signal of the above mentioned selector 68 will be taken out as it is in order to be used for metering. On the other hand, it will have $\gamma$ corrected again by a $\gamma$ correcting circuit 69 and will be output to the monitor in order to be displayed.

A signal processing circuit 70 shown in FIG. 10 is to process signals with software (that is, with a microcomputer), whereas the signal processing circuit 60 shown in FIG. 9 is to make a calculation with hardware. That is to say, the above mentioned signal processing circuit 70 has three memories 71a, 71b and 71c respectively memorizing picture image data corresponding to respective wavelengths within the selected wavelength group so that the data memorized in the respective memories will be input into a micro-processor 72 and predetermined calculations for determining the $SO_2$, blood flow amount and hemoglobin amount will be made with this micro-processor 72.

Figure 6:
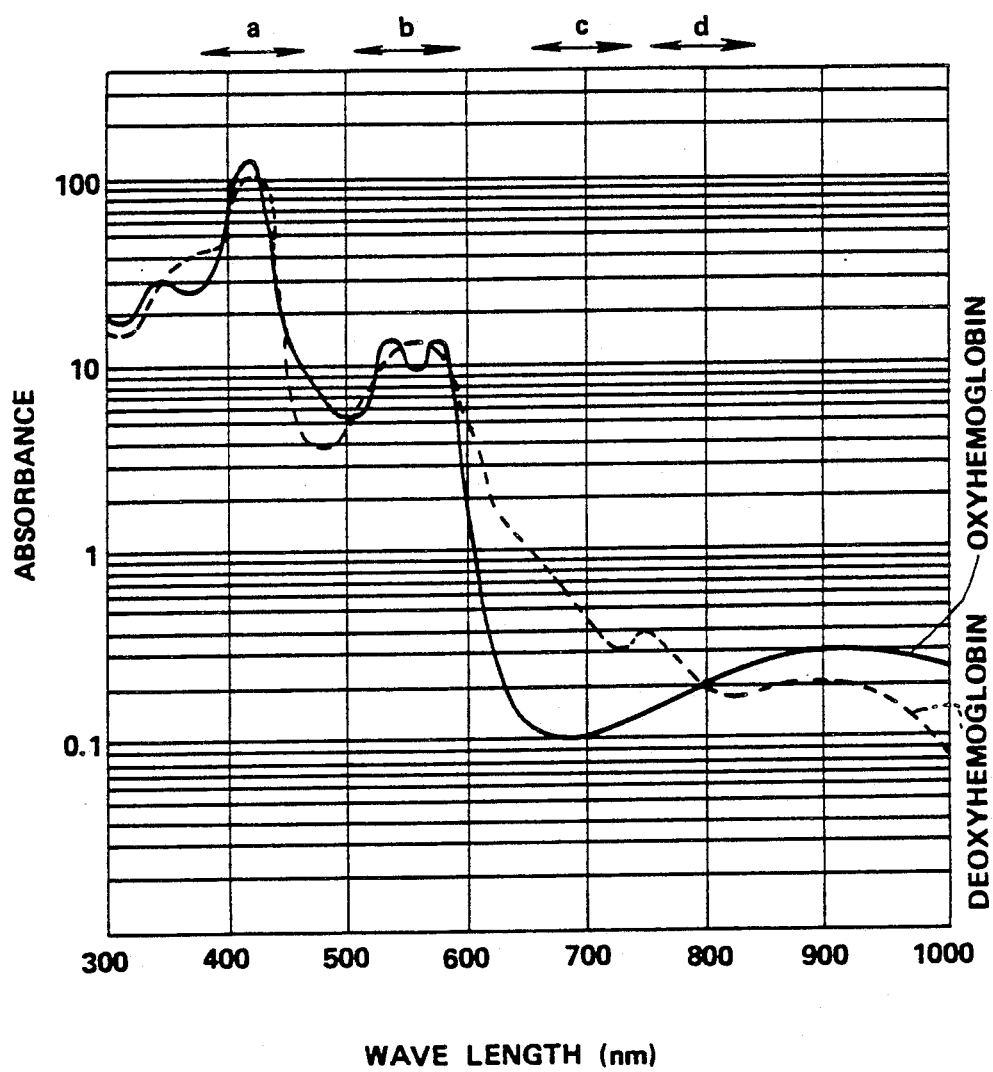

By the way, in the case of observing and measuring a blood flow amount, in FIG. 6, combination of wavelength ranges of a and b, b and c or b and d among respective wavelength ranges represented by a, b, c and d may be used.

Thus, in this embodiment, by varying the positions of the rotary filter 50 and motor 23 with respect to the optical axis of the illuminating light path, the combination of wavelengths separating the illuminating light in time series can be selected from three wavelength groups of (R, G and 'B), ($\lambda 11$, $\lambda 12$ and $\lambda 13$) and ($\lambda 21$, λ22 and λ23). Therefore, by selecting the most suitable wavelength range in response to the observed part and observing object, an ordinary picture image and a picture image showing the variations of the oxygen saturation degree and amount of hemoglobin, the blood flow and the like in the blood in different wavelength ranges can be switched and observed. As the light transmitting characteristics through the mucous membrane are different depending on the respective wavelength groups, the observed or metered picture image will be different by the variation in the thickness direction of the mucous membrane depending on the selected wavelength group. Therefore, for example, by comparing the differences between the picture images showing the $SO_2$ and hemoglobin amounts of respective wavelength groups, the variations of the $SO_2$ and hemoglobin amount on the extreme surface of the mucous membrane to the variations in the interior can be observed and metered and the three-dimensional variations of the $SO_2$ and hemoglobin amount as well as the thickness direction of the mucous membrane can be observed and metered. This has an effect of being useful to the early discovery of a disease and the determination of the penetrating range.

By the way, the number of the wavelength groups provided in the rotary filter 50 is not limited to be three but may be a plurality.

Figure 11:
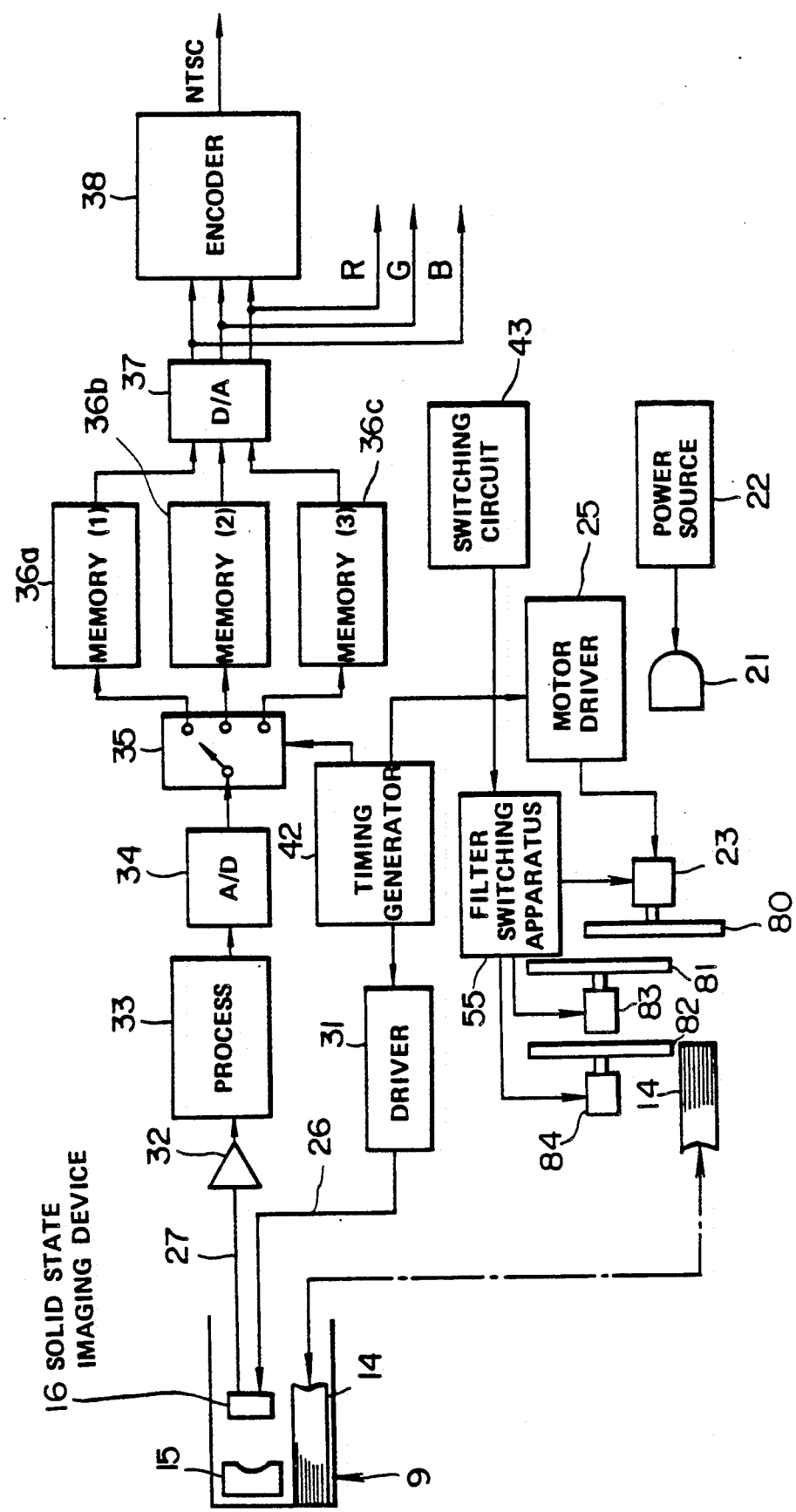

FIGS. 11 to 13 show the second embodiment of the present invention.

In this embodiment, as shown in FIG. 11, instead of the rotary filter 50 in the first embodiment, a rotary filter 80 for the ordinary observation and two rotary filters 81 and 82 for special picture images are provided to be selectively insertable in the illuminating light path. The above mentioned rotary filters 80, 81 and 82 are rotated and driven respectively by motors 23, 83 and 84 and can be moved to be removably inserted in the illuminating light path together with the motors 23, 83 and 84 by the filter switching apparatus 55.

By the way, the motors 83 and 84 are driven respectively by motor drivers not illustrated controlled by the timing generator 42 the same as in the motor 23.

In the above mentioned rotary filter 80 for the ordinary observation, as shown in FIG. 12, filters 80a, 80b and 80c transmitting respectively the lights of the respective wavelength ranges of R, G and B are arranged in the peripheral direction.

On the other hand, in the rotary filters 81 and 82 for special picture images, filters 81a, 81b, 81c, 82a, 82b and 82c transmitting the lights of the narrow bands with wavelengths λ1, λ1 and λ3 respectively as centers are arranged in the peripheral direction. By the way, the combination of the above mentioned wavelengths λ1, λ2 and λ3 may be either of such five wavelength groups of λ11, λ12 and λ13 and the like as are shown in FIG. 5 or may be such combination of wavelength ranges a, b, c and d as is shown in FIG. 6. However, the combinations of the transmitted wavelength ranges of the respective filters are different between the rotary filters 81 and 82.

In this embodiment, by selectively inserting one of the rotary filter 80 for the ordinary observation and two rotary filters 81 and 82 for special picture images into the illuminating light path by the filter switching apparatus 55, an ordinary picture image and a picture image showing the variations of the oxygen saturation degree and amount of hemoglobin and the blood flow amount in a blood in different wavelength ranges can be switched and observed.

By the way, the number of the rotary filters selectively inserted in the illuminating light path is not limit to be three but may be a plurality.

The other formations, operations and effects are the same as in the first embodiment.

FIGS. 14 and 15 show the third embodiment of the present invention.

In this embodiment, a color mosaic system is used for the color imaging system.

As shown in FIG. 14, an electronic endoscope 101 has an objective lens system 108 in the tip part of an insertable part. A beam splitter 109 dividing the light path into two is provided in the light path of this objective lens system. A solid state imaging device 103 having a color filter array 102 for the ordinary observation provided on the front surface is arranged in the image forming position of one light path divided by the above mentioned beam splitter 109. A solid state imaging device 113 having a color filter array 112 for special picture images provided on the front surface is arranged in the image forming position of the other light path divided by the above mentioned beam splitter 109.

A light source part 104 contained in the video processor 6 has a lamp 105 emitting a light in a wide band from an ultraviolet light to an infrared light. The light emitted from this lamp 105 will be condensed by a lens 106 and will enter a light guide 107 at the entrance end.

As shown in FIG. 15, the above mentioned color filter array 102 for the ordinary observation is formed by mosaic-like arranging filters transmitting lights of respective wavelength ranges, for example, of green (G), cyanine (Cy) and yellow (Ye). By the way, an infrared cutting filter may be provided together with the above mentioned color filter array 102 on the front surface of the solid state imaging device 103.

On the other hand, in the above mentioned color filter array 112 for special picture images, the arrangement is the same as in the above mentioned color filter array 102 but filters transmitting the lights of narrow bands with wavelengths λ1, λ2 and λ3 as centers instead of G, Cy and Ye are arranged. By the way, the combination of the above mentioned wavelengths λ1, λ2 and λ3 may be any of such five wavelength groups of λ11, λ12 and λ13 and the others as are shown in FIG. 5 and may be such combination of wavelength ranges a, b, c and d as is shown in FIG. 6.

The image of the object illuminated by the above mentioned illuminating light will be formed on the imaging surfaces of the solid state imaging devices 1-3 and 113 by the objective lens 108. In such case, the image will be separated into colors of G, Cy and Ye by the color filter array 102 on the solid state imaging device 103 side and into λ1, λ2 and λ3 by the color filter array 112 on the solid state imaging device 113 side.

The above mentioned solid state imaging devices 103 and 113 will be read out by applying driving signals respectively of the drivers 120 and 121. One of the output signals of the above mentioned solid state imaging devices 103 and 113 will be selected by the selector 122 and will be passed through low pass filters (LPF's) 123 and 124 and a band pass filter (BPF) 125 within the video processor 6. By the way, the above mentioned selector 122 will switch the selected signal by a switching signal from a switching signal generating circuit not illustrated.

The above mentioned LPF's 123 and 124 show cut-off characteristics, for example, of 3 MHz and 0. MHz. The signal having passed through them will be divided into a luminance signal YH of a high range and a luminance signal YL of a low range which will be input respectively into processing circuits 126 and 127 and will have γ corrected. The high range side luminance signal YH having passed through the above mentioned processing circuit 126 will have the horizontal outline and horizontal aperture corrected by a horizontal correcting circuit 128 and then will be input into a color encoder 129. The low range side luminance signal YL having passed through the processing circuit 127 will be input into a matrix circuit 131 and into a correcting circuit 133 to have the tracking corrected.

On the other hand, a color signal component will be extracted through the BPF of a passing band of 3.5±0.5 MHz and will be input into a 1 HDL (1 H delay line) 134, adder 135 and subtractor 136 and color signal components B and R will be separated and extracted. By the way, in this case, the output of the 1 HDL 134 will be mixed in a mixer 138 with the low range side luminance signal YL processed in the processing circuit 127 and further having had the vertical aperture corrected in the vertical correcting circuit 137 and this mixed output will be input into the above mentioned adder 135 and subtractor 136. The color signal B of the adder 135 and the color signal R of the subtractor 136 will be input respectively into γ correcting circuits 141 and 142, will have γ corrected by using the low range side luminance signal Y having passed through the correcting circuit 133, will be input respectively into demodulators 143 and 144 and will be made demodulated color signals B and R which will be then input into a matrix circuit 131. Color difference signals R-Y and B- will be produced by this matrix circuit 131 and then will be input into a color encoder 129. A luminance signal made by mixing the luminance signals YH and YL and a chromatic signal made by intersecting at right angles and modulating color difference signals R-Y and B-Y with a sub-carrier will be mixed together (further a synchronous signal not illustrated will be superimposed) and a composite video signal will be output from an NTSC output end 145. The observed par will be video-displayed in colors by the video signal output out of this output end 145.

By the way, synchronous signals will be input into the drivers 120 and 121 from a synchronous signal generating circuit 152 and driving signals synchronized with these synchronous signals will be output. The output of this synchronous signal generating circuit 152 will be input into a pulse generator 153 and various timing pulses will be output from this pulse generator 153.

In this embodiment, by switching and processing the signal imaged by the solid state imaging device 103 for the ordinary observation and the signal imaged by the solid state imaging device 113 for special picture images, the ordinary picture image and the picture image showing the variations of the oxygen saturation degree and amount off hemoglobin and the blood flow amount in a blood can be switched and observed.

The other formations, operations and effects are the same as in the first embodiment.

Figure 16:
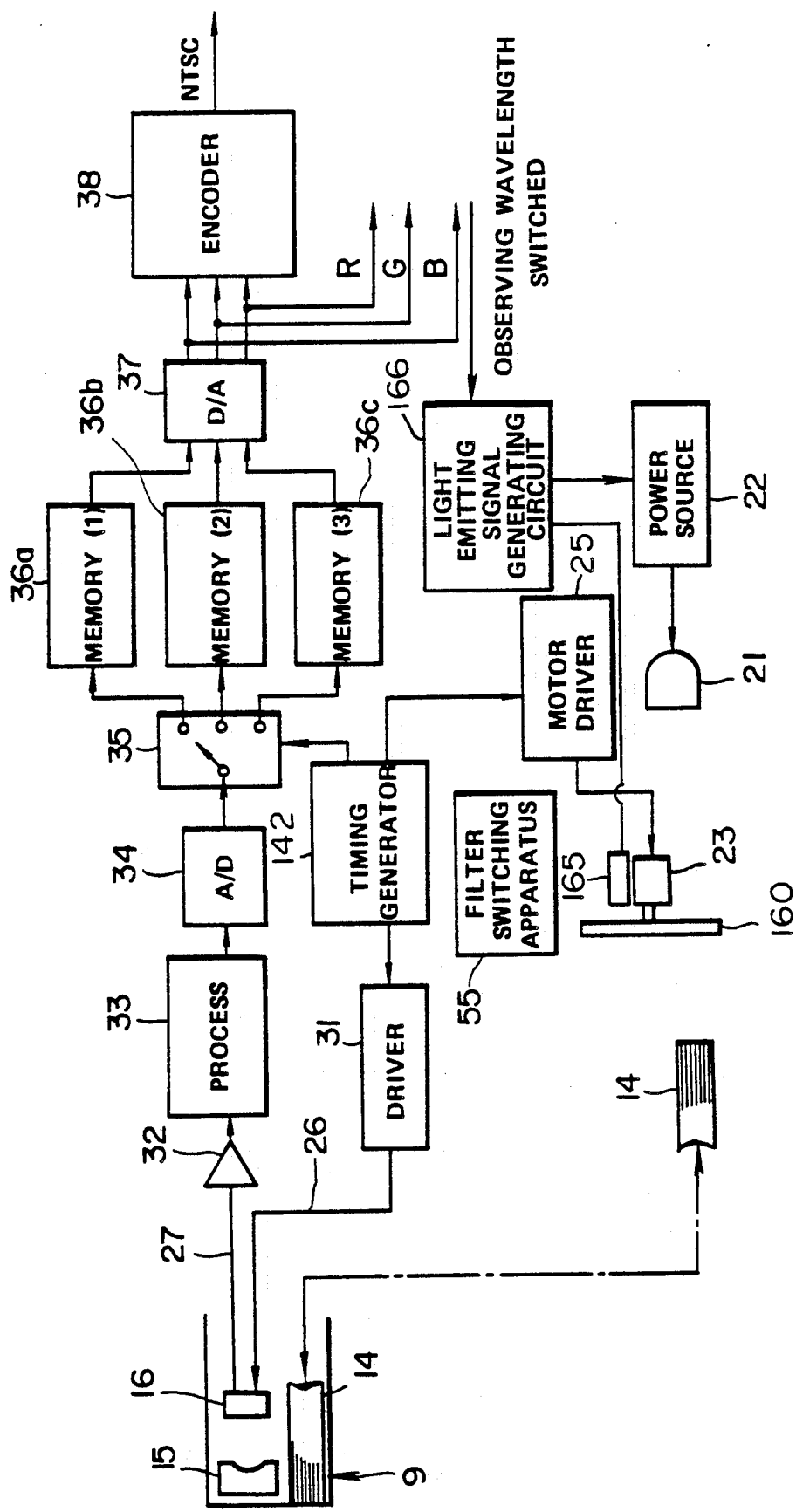
FIG. 16 and 17 relate to the fourth embodiment of the present invention.
Figure 17:
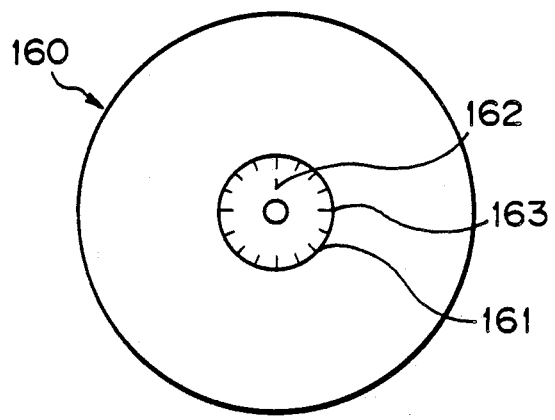

FIGS. 16 and 17 show the fourth embodiment of the present invention.

In this embodiment, instead of the rotary filter 50 in the first embodiment, as shown in FIG. 16, a linear interfering filter 160 is provided. In this linear interfering filter 160, a main wavelength of a band pass characteristic of a narrow band continuously varies with the peripheral position. This linear interfering filter 160 is rotated by the motor 23.

As shown in FIG. 17, a reflecting plate 161 for an encoder is provided in the center part of the above mentioned linear interfering filter 160. A starting position detecting mark 162 and a plurality of rotating position detecting marks 163 are formed in this reflecting plate 161 for the encoder. The rotating position of the above mentioned linear interfering filter 160 can be detected by an encoder 165 detecting these marks 162 and 163. The detecting output of the above mentioned encoder 165 will be input into a light emitting signal generating circuit 166. When the part transmitting the wavelength required for the observation in the above mentioned linear interfering filter 160 is interposed in the illuminating light path in response to the observing wavelength switching signal from an observing wavelength setting means not illustrated, this light emitting signal generating circuit 166 will transmit a light emitting signal instructing to emit a light to the power source 22 feeding an electric power to the light source 21. When the part transmitting the wavelength required for the observation in the above mentioned linear interfering filter 160 is interposed in the illuminating light path, the above mentioned lamp 21 will flash.

Thus, in this embodiment, by selecting any plurality of wavelength ranges in the linear interfering filter 160, an ordinary picture image and a picture image showing the variations of the oxygen saturation degree and amount of hemoglobin and the blood flow amount, in a blood in different wavelength ranges can be switched and observed.

Also, according to this embodiment, as different from the first to third embodiments, the combination of the observing wavelength ranges can be freely selected and therefore the observation can be made by the combination of more wavelength range.

The other formations, operations and effects are the same as in the first embodiment.

Figure 18:
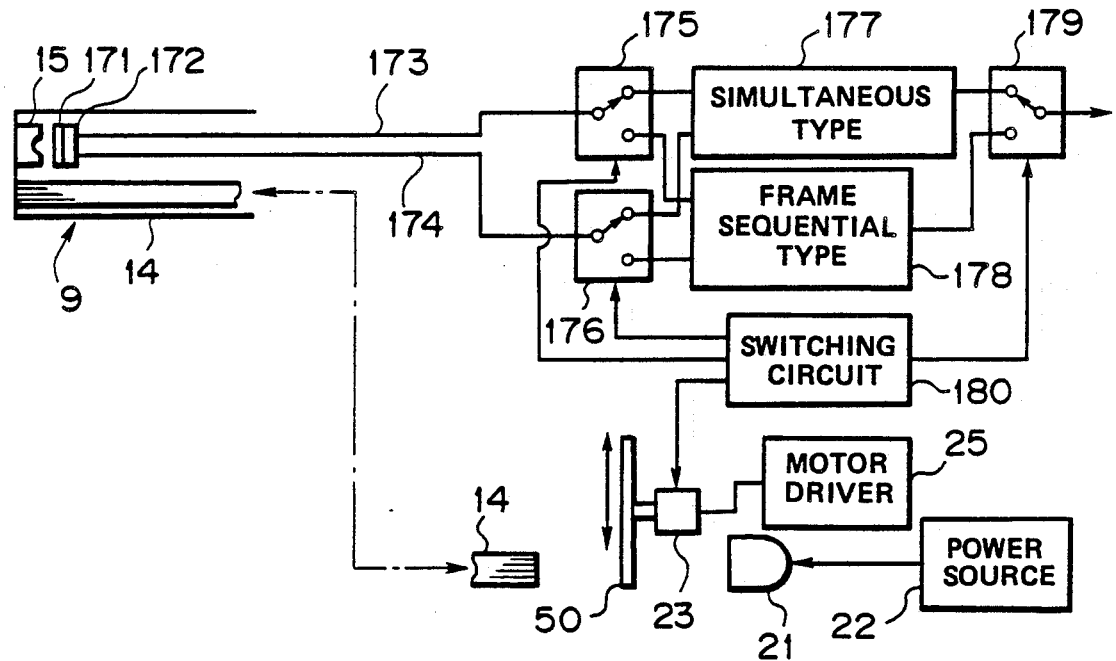
FIG. 18 is a block diagram showing the formation of an endoscope apparatus of the fifth embodiment of the present invention.

FIG. 18 shows the fifth embodiment.

In this embodiment, a solid state imaging device 172 provided on the front surface with the same ordinary observation collar filter array 171 as is shown in FIG. 15 is arranged in the image forming position of the objective lens system 15 in the tip part 9 of the insertable part of the electronic endoscope. A driving pulse transmitting signal line 173 and output signal transmitting signal line 174 are connected to this solid state imaging device 172 and are connected respectively to a simultaneous type signal processing circuit 177 and frame sequential type signal processing circuit 178 respectively through selectors 175 and 176. One of the output signal of the above mentioned simultaneous type signal processing circuit 177 and the output signal of the frame sequential type signal processing circuit 178 will be selected by a selector 179 and will be output to a signal processing circuit in the later step. By the way, the above mentioned selectors 175, 176 and 179 will be switched by a switching circuit 180 all on the simultaneous type side or the frame sequential type side.

On the other, the same rotary filter 50 as in the first embodiment is provided in the light source part. This rotary filter 50 and the motor 23 can be displaced with respect to the optical axis of the illuminating light path by the above mentioned switching circuit 180. By the way, in this embodiment, the above mentioned rotary filter 50 can be retreated perfectly from the illuminating light path.

In this embodiment, in the case of the ordinary color observation, when the rotary filter 50 is retreated perfectly from the illuminating light path, the illuminating light is color-separated by the color filter array 171, the simultaneous type signal processing circuit 177 side is selected and the signal is processed in the simultaneous type, a color picture image will be obtained.

On the other hand, in the case of observing the variations of the oxygen saturation degree and amount of hemoglobin and the blood flow amount in a blood when the above mentioned rotary filter 50 is interposed in the illuminating light path, the illuminating light is color-separated in time series and the frame sequential type signal processing circuit 17 side is selected and the signal is processed in the frame sequential type, a color picture image will be obtained.

By displacing the above mentioned rotary filter 50 with respect to the optical axis of the illuminating light path, any wavelength group can be selected from a plurality of wavelength groups. By the way, in this embodiment, at the time of the ordinary observation, the color separation will be made with the color filter array 171. Therefore, the above mentioned rotary filter 50 is not required to be provided with such ordinary observation filters as of R, G and B.

Also, in case the wavelength range for special picture images includes an infrared light and ultraviolet light, when, for example, the transmitted wavelength range of the Cy transmitting filter of the above mentioned color filter array 171 is expanded to the ultraviolet band and the transmitted wavelength range of the Ye transmitting filter is expanded to the infrared band, the observation will be possible. By the way, in this case, at the time of the ordinary observation, an infrared cutting filter and ultraviolet cutting filter may be inserted. The other formations, operations and effects are the same as in the first embodiment.

FIGS. 19 to 22 show the sixth embodiment of the present invention.

In this embodiment, the solid state imaging device is provided on the imaging surface with an intercepting means intercepting the light so that the wavelength range including an ultraviolet light, visible light and infrared light may be selected in response to an object to be observed and a video information may be obtained. The tone difference in the respective parts of the observed object difficult to discriminate in the general visible range picture image can be detected.

Figure 19:
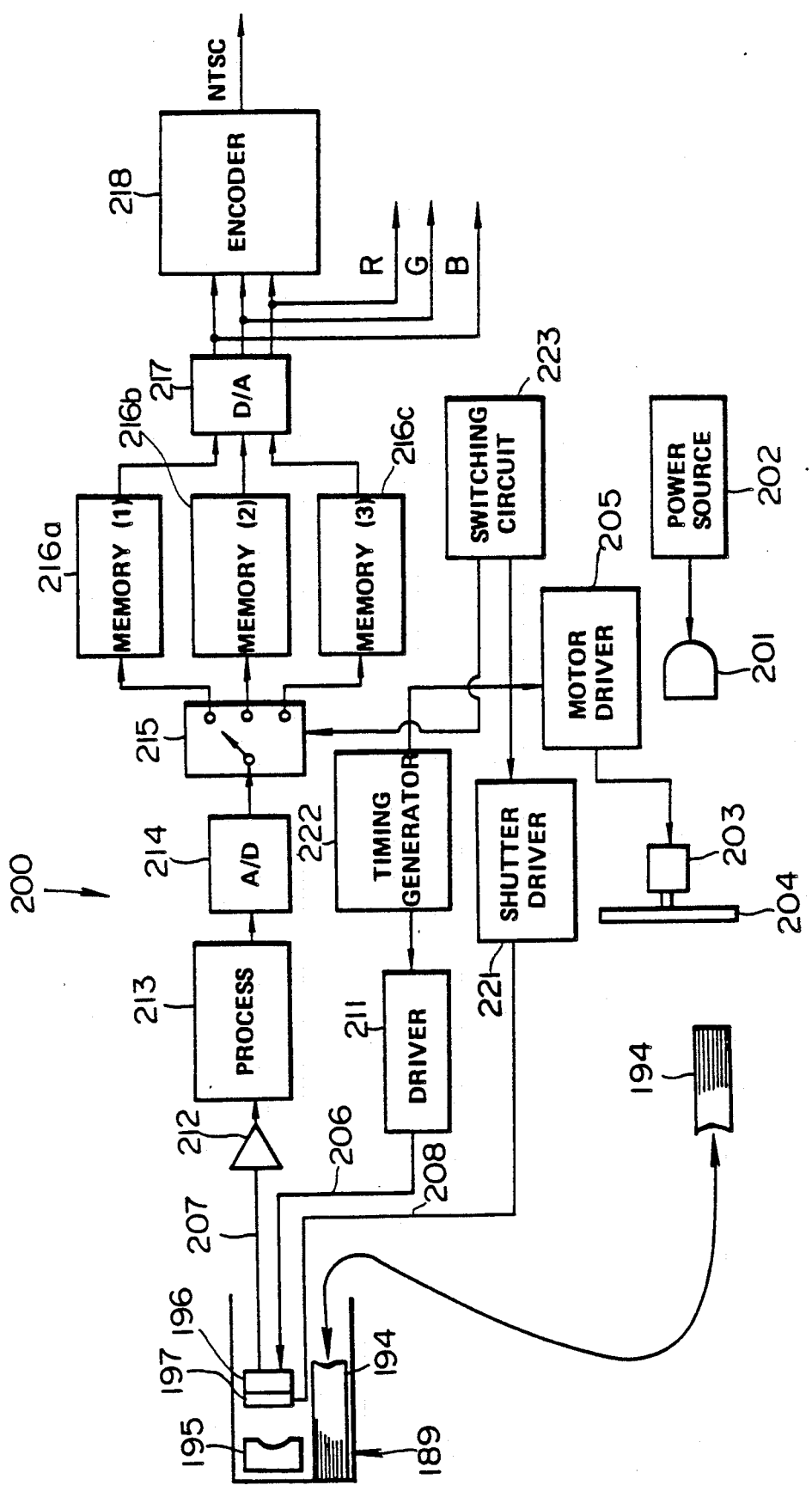
FIG. 19 to 22 relate to the sixth embodiment of the present invention.

The electronic endoscope apparatus 200 of this embodiment is formed as shown in FIG. 19.

A light guide 194 transmitting an illuminating light is inserted through an insertable part 182 of an endoscope 181 and is arranged on the tip surface in the tip part 189 of the above mentioned insertable part 182 so that an illuminating light may be emitted from this tip part 189. The above mentioned light 194 is inserted on the entrance end side through the universal cord 14 and is connected to the above mentioned connector 185. An objective lens system 195 is provided in the above mentioned tip part 189. A solid state imaging device 196 is arranged in the image forming position of this objective lens system 195, has a sensitivity in a wide wavelength range including a visible range and ranging from an ultraviolet range to an infrared range and is provided on the front surface with a liquid shutter 197 temporarily intercepting the light entering it. Signal lines 206 and 207 are connected to the above mentioned solid state imaging device 196. A signal line 20 is connected to the above mentioned liquid crystal shutter 197. These signal lines 206, 207 and 20 are inserted through the above mentioned insertable part 182 and universal cord 184 and are connected to the above mentioned connector 185.

Figure 20:
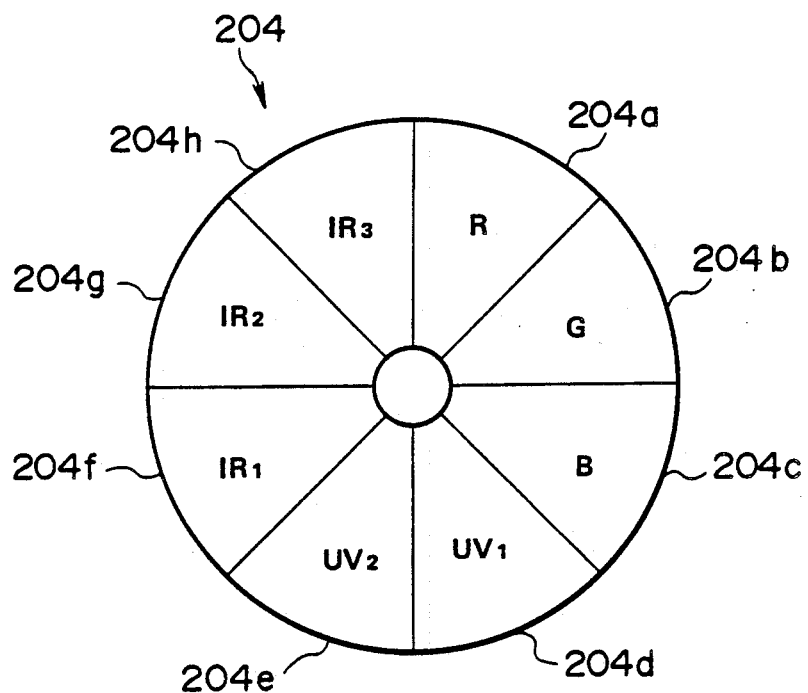
Figure 21:
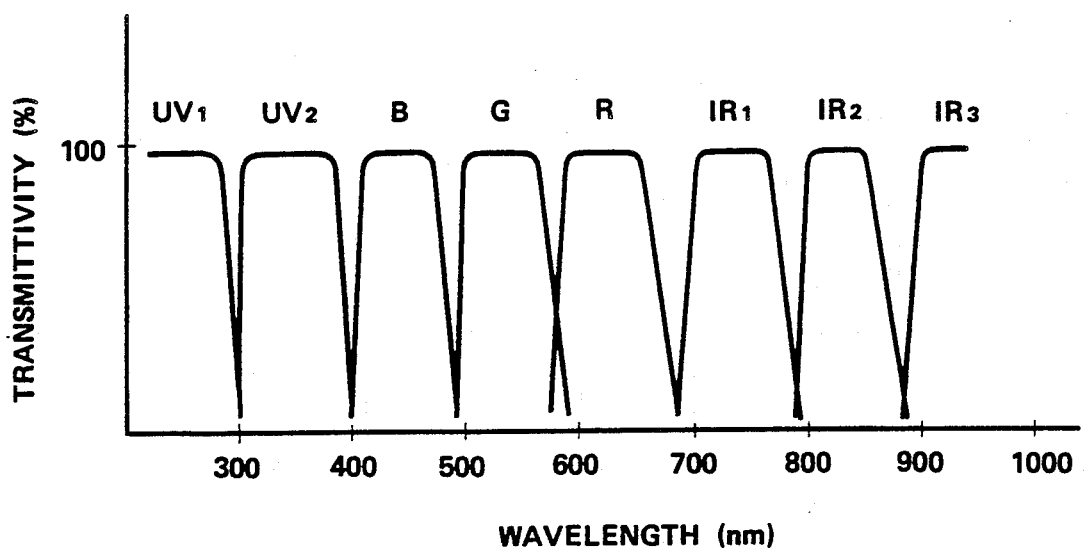

On the other hand, a lamp 201 emitting a light in a wide band from an ultraviolet light to an infrared light is provided within a control apparatus 16. A general xenon lamp or strobo-lamp can be used for this lamp 201. The above mentioned xenon lamp or strobo-lamp emits a large amount of not only a visible light but also an ultra violet light and infrared light. This lamp 201 is fed with an electric power by a light source part 202. A rotary filter 204 as a dividing means rotated and driven by a motor 203 is arranged forward of the above mentioned lamp 201 and is divided into eight parts in the peripheral direction as shown in FIG. 20. In the divided respective parts, as shown in FIG. 21, filters 204a to 204h having band pass characteristics of selectively transmitting wavelengths of narrow bands ranging from an ultraviolet light range to an infrared light range and transmitting respectively the lights of red (R), green (G), blue (B), first ultraviolet (UV1), second ultraviolet (UV2), first infrared (IR1), second infrared (IR2) and third infrared (IR3) are arranged in the order mentioned. By the way, the above mentioned first to third infrared lights are different in the wavelength ranges and are longer in the wavelengths in the order of IR1, IR2 and IR3. Likewise, the above mentioned first to second ultraviolet lights are different in the wavelength ranges and are longer in the wavelengths in the order of UV1 and UV2. The above mentioned motor 203 is controlled in the rotation and driven by a motor driver 205.

The light having passed through the above mentioned rotary filter 204 will enter the above mentioned light guide 194 at the entrance end, will be led to the tip part 189 through this light guide 194 and will be emitted from this tip part 19 to illuminate a part to be observed.

The returning light from this observed part by this illuminating light will be made to form an image on the solid state imaging device by the objective lens system 195 and will be photoelectrically converted. A driving pulse from the driver circuit 211 within the above mentioned control apparatus 16 will be applied to this solid state imaging device 196 through the above mentioned signal line 206. The reading-out and transfer will be made by this driving pulse. The video signal read out of this solid state imaging device 196 will be input into a pre-amplifier 212 provided within the above mentioned control apparatus 186 or electronic endoscope 181. The video signal amplified by this pre-amplifier 212 will be input into a processing circuit 213, will be processed to have γ corrected and white balanced and will be converted to a digital signal by an A/D converter 214. This digital video signal will be selectively memorized in three memories (1) 216a, (2) 216b and (3) 216c corresponding to the respective colors, for example, of red (R), Green (G) and blue (B) by a selecting circuit 215. Signals will be simultaneously read out of the above mentioned memories (1) 216a, (2) 216b and (2) 216c, will be converted to analog signals by a D/A converter 217 and will be output as R, G and B color signals and, at the same time, will be input into an encoder 21 and will be output out of this encoder 21 as an NTSC composite signal.

The above mentioned R, G and B color signals or NTSC composite signal will be input into the color monitor 7 and the observed part will be displayed by this color monitor 7.

The above mentioned liquid crystal shutter 197 is connected to a shutter driver 221 within the above mentioned control apparatus 186 through the signal line 20 so as to be opened and closed by this shutter driver 221.

A timing generator 222 making a timing of the entire system is provided within the above mentioned control apparatus 186. The respective circuits of the motor driver 205 and driver circuit 211 will be synchronized by this timing generator 222.

A switching circuit 223 controlling the shutter driver 221 to be synchronized with the above mentioned timing generator 222 so that the light may enter the solid state imaging device 196 only when illuminated through the filter in any transmitted wavelength range selected by the operator in the above mentioned rotary filter 204 is provided within the above mentioned control apparatus 186. This switching circuit 223 will control the above mentioned selecting circuit 215 to memorize in the respective different memories 216a to 216c the video signals corresponding to the respective wavelength range selected by the liquid crystal shutter 197 driven by the above mentioned shutter driver 223. Further, the above mentioned switching circuit 223 will control the power source part 202 to attenuate the emitted light amount of the lamp 201 when the above mentioned liquid crystal shutter 197 is closed and the solid state imaging device 196 receivers no light.

The operation of this embodiment formed as in the above shall be explained in the following.

When the lamp 201 emits a light and the rotary filter 204 is rotated by the motor 203 in the light path of the light of this lamp 201, the light in the wavelength ranges of a wide band from an ultraviolet light to an infrared light emitted from the above mentioned lamp 201 will pass in turn through the respective filters 204a to 204h of the above mentioned rotary filter 204 and will be color-separated in time series into lights of the wavelength ranges shown in FIG. 21. These lights will be radiated through the light guide 194 to a part to be observed from the tip part 189 of the insertable part 12 of the electronic endoscope 11 inserted into a body cavity. The returning lights from the observed part by these illuminating lights will be made to form an image on the solid state imaging device 196.

Here, when, for example, three optional wavelength ranges are selected from among the wavelength ranges divided as shown in FIG. 3 by a switching circuit 223, when the filters corresponding to the selected wavelength ranges among the respective filters 204a to 204h of the above mentioned rotary filter 204 are inserted into the illuminating light path, by the driving of the shutter driver 221, the liquid crystal shutter 197 will open, the above mentioned solid state imaging device 196 will be exposed to the lights and video signals will be obtained. On the other hand, when the filters corresponding the wavelength ranges not selected are inserted into the illuminating light path, the above mentioned liquid crystal shutter 197 will close and the above mentioned solid state imaging device 196 will not be exposed. Thus, only the video images of the observed object illuminated by the lights having passed through the filters corresponding to the wavelength ranges selected by the switching circuit 223 among the respective filters 204a to 204h of the rotary filter 204 will be read out in time series by the driver circuit 211 synchronized with the timing generator 222. The signals read out of this solid state imaging device 196 will be amplified by the pre-amplifier 212, will be processed to have γ corrected and white balanced in a processing circuit 213 and then will be converted to digital signals by the A/D converter 214 and the video signals read out in time series by the selecting circuit 215 will be memorized for the respective wavelength ranges in the memories (1) 216a, (2) 216b and (3) 216c corresponding to the respective colors of R, G and B. The signals simultaneously read out of these memories 216a, 216b and 216c will be converted to analog signals by the D/A converter 217 and will be output as R, G and B signals to the color monitor 7 in which R, G and B signals can be input, the respective colors of R, G and B will be allotted respectively freely to the selected wavelength ranges and the observed object will be displayed in quasi colors. Also, the above mentioned R, G and B signals will be converted to an NTSC composite signal by the encoder 218, will be input into the color monitor 7 and likewise the observed obJect will be displayed in quasi colors. By the way, in case the respective transmitted wavelength ranges of R, G and B are selected and the respective colors of R, G and B are allotted respectively to the respective transmitted wavelength ranges of R, G and B, an ordinary color picture image will be obtained.

As synchronized with the timing generator 222, the above mentioned switching circuit 223 will reduce the emitted light amount of the lamp 201 while the liquid crystal shutter 197 is closed but will increase the emitted light amount of the lamp 201 while the liquid crystal shutter 197 is opened.

Thus, according to this embodiment, in the range of not only a visible light range but also from an infrared light range to an infrared light range, any wavelength ranges are selected from among the wavelength ranges divided as shown in FIG. 21, the observed object can be color-displayed by allotting any colors and the optimum observing wavelength band can be selected.

Therefore, the tone difference of the respective parts of the observed object difficult to discriminate in the general visible range picture image can be easily detected and a disease part can be easily detected.

Figure 22:
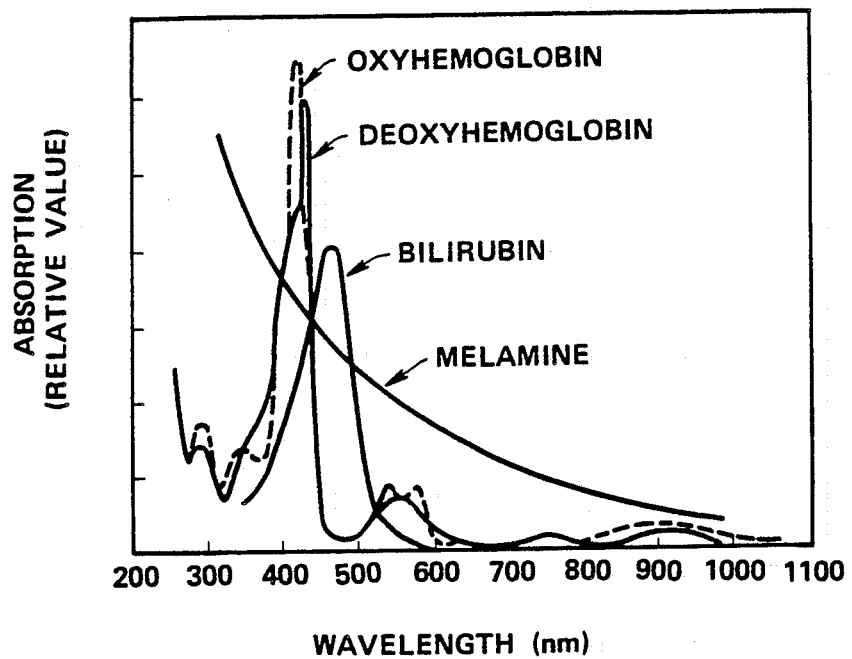

By selecting a wavelength range including different absorption peaks for respective colors of a living body as shown, for example, in FIG. 22 or a wavelength range in which the absorption rate difference from other colors in largest, the color distribution in the living body tissue can be detected.

Further, by using a light in a long wavelength range above 600 nm. high in the permittivity through a living body, the vein running and disease penetrating range below the mucous membrane can be easily observed. Thus, according to this embodiment, there is an effect that the diagnosing activity can be improved.

By the way, the solid state imaging device 196 may be provided with a transferring light intercepting part or no light intercepting part.

Figure 23:
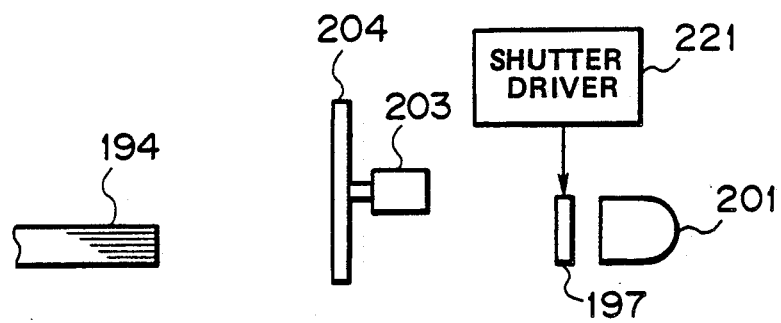
FIGS. 23 to 25 relate to a modification of the sixth embodiment.
Figure 24:
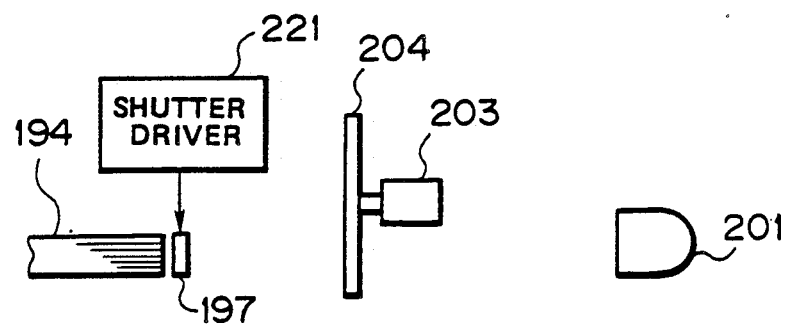
Figure 25:
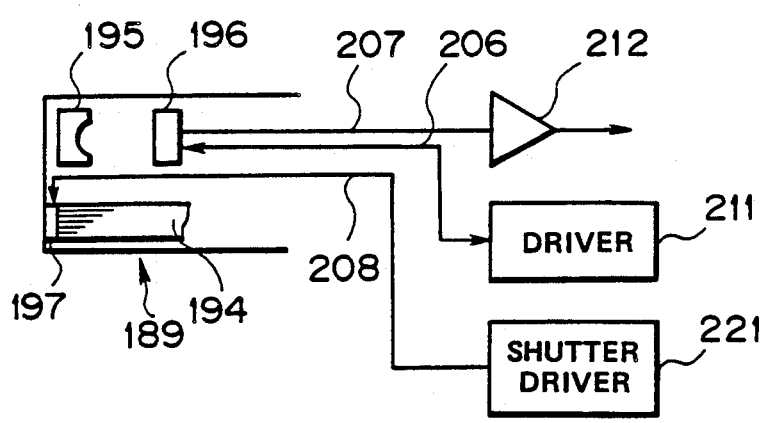

By the way, the liquid crystal shutter 197 is not limited to be positioned on the front surface of the solid state imaging device 196 but may be between the lamp 201 and solid state imaging device 196 and may be provided on the front surface of the lamp 201 as shown, for example, in FIG. 23, at the entrance end of the light guide 194 as shown in FIG. 24 or at the exit end of the light guide 194 as shown in FIG. 25.

Figure 26:
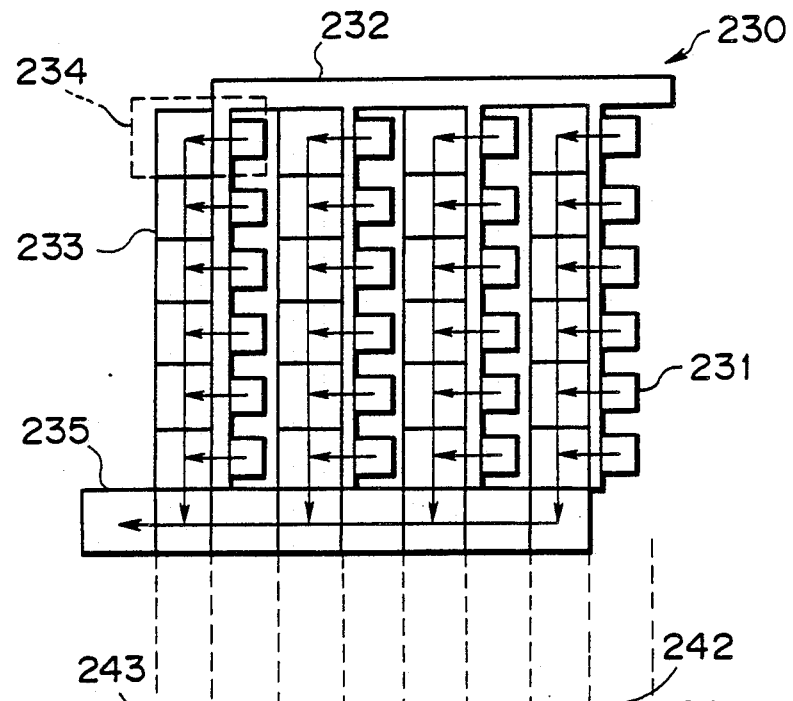
FIGS. 26 and 27 relate to the seventh embodiment of the present invention.
Figure 27:
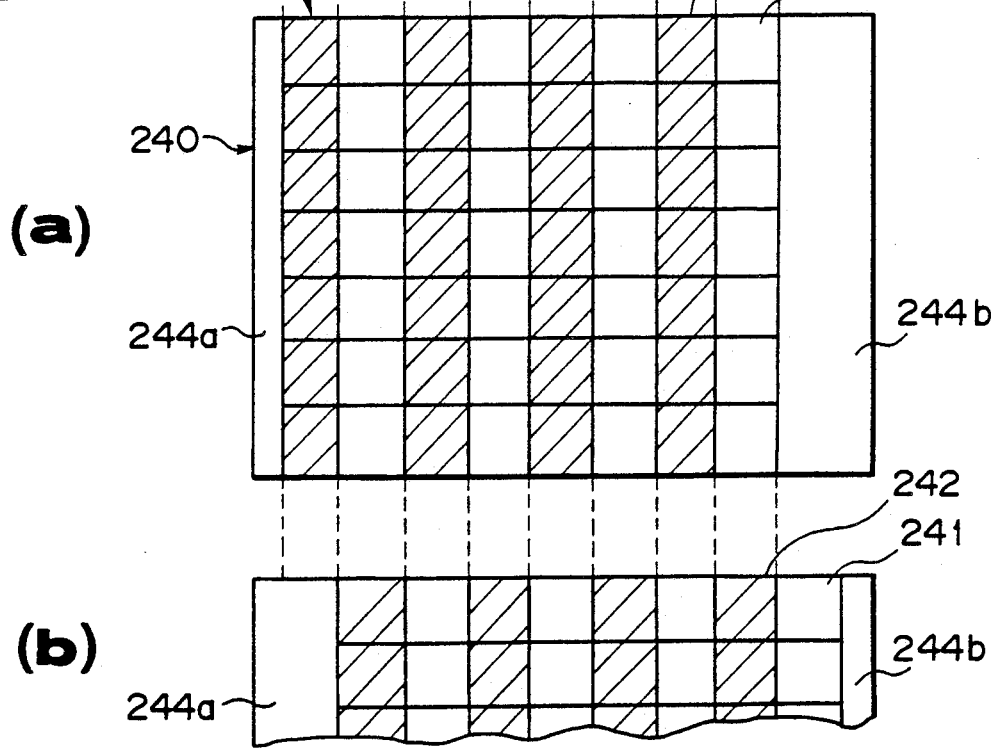
Figure 28:
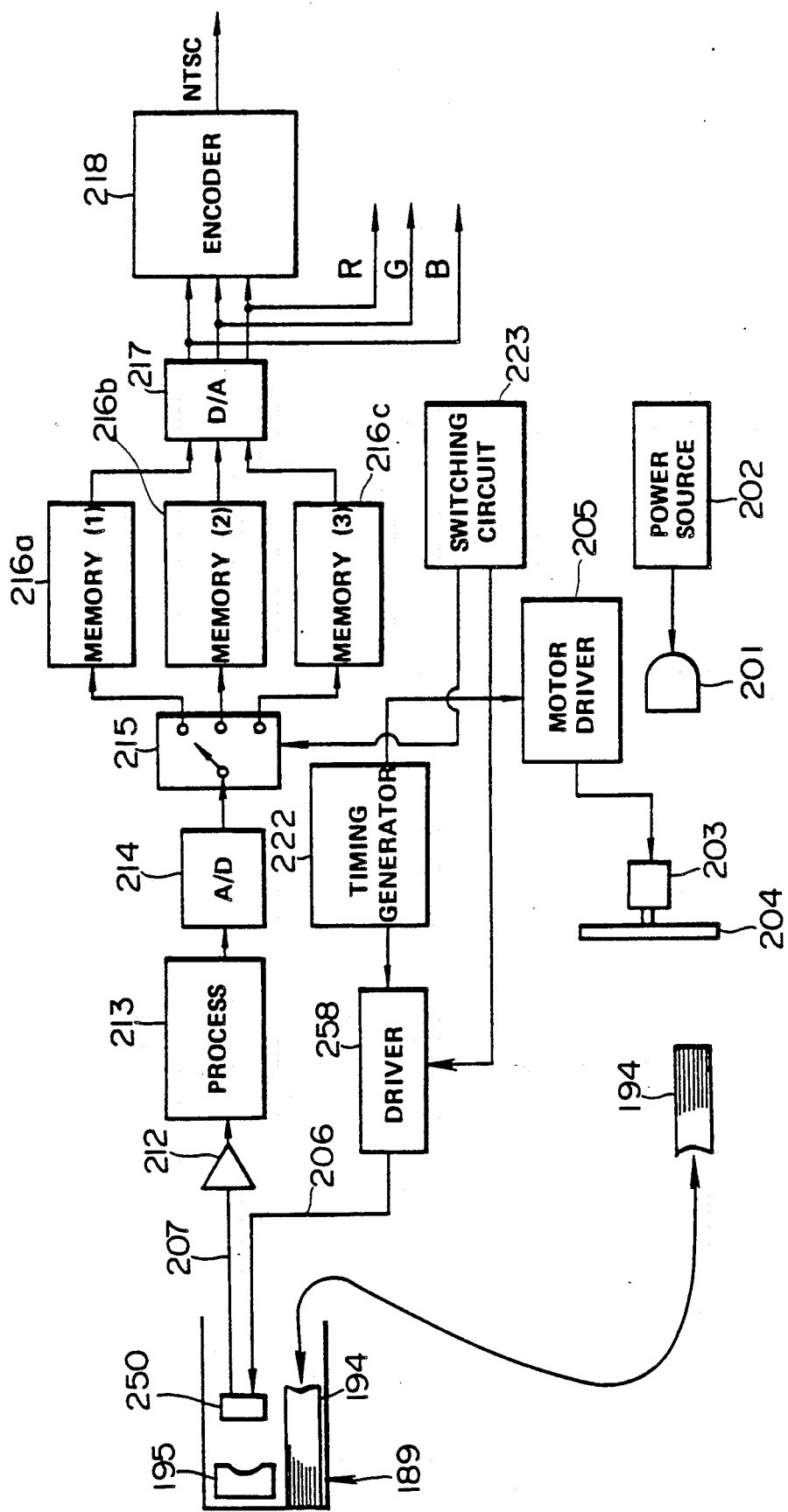

FIGS. 26 and 27 show the seventh embodiment of the present invention.

In this embodiment, the solid state imaging device 196 in the sixth embodiment is made an interline type CCD 230 and a shutter 240 using a piezoelectric device is provided instead of the liquid crystal shutter 197.

As shown in FIG. 26, the above mentioned CCD 230 has one pixel 234 formed of a photosensitive part 321 receiving a light and photoelectrically converting it to an electric signal, a reading-out gate 232 reading out a signal charge accumulated in this photosensitive part and a vertically transferring CCD 233 transferring vertically the signal charge read out of this reading-out gate 232 and is provided with a horizontally transferring CCD 235 transferring horizontally the electric charge transferred by the above mentioned vertically transferring CCD 233. By the way, the rate occupied by the above mentioned light receiving part 231 in the entire CCD 230 is less than 50% because there are the reading-out gate 232 and vertically transferring CCD 233.

On the other hand, the above mentioned shutter 240 is arranged on the front surface of the above mentioned CCD 230 and is formed of a filter 243 dividing the width of on pixel 234 of the above mentioned CCD 230 into two parts and arranging a transmitting part 241 in one part and a light intercepting part 242 in the other part and piezoelectric devices 244a and 244b fitted to both end parts of the direction of arranging the transmitting parts 241 and light intercepting parts 242. The above mentioned piezoelectric devices 244a and 244b are driven by a shutter drive 221 so that, when one contracts, the other will extend and thereby the above mentioned filter 243 will able to be parallelly moved in the horizontal direction by half the pixel. The transmitting part 241 can be switched to be positioned on the photosensitive part 231 of the CCD 230 as shown in FIG. 27 (A) and the light intercepting part 242 can be switched to be positioned on the above mentioned photosensitive part 231 as shown in FIG. 27 (b).

The other formations are the same as in the sixth embodiment.

In this embodiment, the same as in the sixth embodiment, the light emitted from the lamp 201 will be color-separated in time services by the rotary filter 204 and will be radiated to a part to be observed through the light guide 194. The returning light from this observed part will be made to form an image on the above mentioned CCD 230 by the objective lens system 195.

Here, when any wavelength range is selected from among the wavelength ranges divided as shown in FIG. 21 by the switching circuit 223, when the filter corresponding to the selected wavelength range among the respective filters 204a to 204h of the above mentioned rotary filter 204 is inserted into the illuminating light path, the piezoelectric devices 244a and 244b will be driven by the shutter driver 221 and the transmitting part 241 will be positioned on the photosensitive part 231 to expose the part 231 as shown FIG. 27 (a). On the other hand, when the filter corresponding to the wavelength range not selected is inserted into the illuminating light path, as shown in FIG. 27 (b), the light intercepting part 242 will be positioned on the above mentioned photosensitive part 231 not to expose the part 231.

Thus, according to this embodiment, the same as in the sixth embodiment, only the video images of the observed object illuminated by the lights having passed through the filters corresponding to the wavelength ranges selected by the switching circuit 23 among the respective filters 204a to 204h of the rotary filter 204 will be read out in time series.

Also, in the embodiment, without perfectly switching the transmitting pat 241 and light intercepting part 242 of the above mentioned shutter 240, the transmitting part 241 and light intercepting part 242 may be arranged at any ratio on the photosensitive part 231 of the CCD so that the shutter 240 may have the same function as of the iris. Therefore, in such case that the reflection factor of the mucous membrane tissure in the respective wavelength ranges is extremely different, the video image in the respective wavelength ranges can be made proper.

The other operations and effects are the same as in the first embodiment.

FIGS. 28 to 31 show the eighth embodiment of the present invention.

In this embodiment, a CCD 250 fitted with an electronic shutter is used instead of the solid state imaging device 196, liquid crystal shutter 197 and shutter driver 221 in the sixth embodiment.

As shown in FIG. 29, the above mentioned electronic shutter fitted CCD 250 comprises an imaging part 253 formed of a light receiving parts 251 photoelectrically converting an optical picture image to a video signal and a vertically reading-out register 252 reading out an electric charge of this light receiving part 251; an accumulating part 254 accumulating video signals of respective lines of the above mentioned vertically reading-out register 252; a horizontally reading-out register 255 reading out as a video signal the electric charge accumulated in the above mentioned accumulating part 254; and an electric charge absorbing drain 256 absorbing unnecessary electric charges read out in the above mentioned vertically reading out register 252.

The above mentioned electronic shutter fitted CCD 250 is driven by a driven circuit 258.

In this embodiment, the same as in the sixth embodiment, the light emitted out of the lamp 201 will be color-separated in time series by the rotary filter 204 and will be radiated to a part to be observed through the light guide 194. The returning lights from this observed part will be made to form an image on the above mentioned electronic shutter fitted CCD 250.

Here, the driver circuit 258 which is a driving circuit of the above mentioned electronic shutter fitted CCD 250 operates as shown in FIGS. 30 and 31. By the way, the drawings show an example of the case of quasi-colorizing the video images of the respective wavelength ranges of G, IR2 and UV1.

The same as in the sixth embodiment, as shown in FIG. 31 (a), the light emitted from the lamp 201 will be color-separated into the respective wavelength ranges of R, G, B, IR1, IR2, IR3, UV1 and UV2 and will be radiated to a part to be observed through the light guide 194. The returning lights from this observed part will be made to form an image on the above mentioned electronic shutter fitted CCD 250 by the objective lens system 195. In the case of quasi-colorizing the video images of the respective wavelength ranges of G, IR2 and UV1, first of all, as shown in (A) in FIG. 31 (b), just before the illumination by the required G filter is made, as shown in FIG. 31 (c), the video signal by the illuminating light having passed through the other filters and accumulated until then in the light receiving part will be read out in the vertically reading-out register 252 as an unnecessary electric charge from the light receiving part 251. This shall be temporarily called art (A) mode. Then, until a pre-determined time during the illumination by the G filter shown in (B) in FIG. 31 (b), the above mentioned vertically reading-out register 252 will transfer the unnecessary electric charge to the electric charge absorbing drain 256. On the other hand, as shown in FIGS. 30 (b) and 31 (c), the light receiving part 251 having read out the unnecessary electric charge in the above mentioned (A) mode will accumulate a video information by the illuminating light having passed through the required G filter. Then, the signal electric charge accumulated in the above mentioned light receiving part 251 will be read out in the vertically reading-out register 252 and will be accumulated in the accumulating part 254. When the signal electric charge is transferred to the accumulating part 254 from the imaging part 253 as shown in FIG. 30 (c) until the pre-determined time shown in (c) in FIG. 31 (c), it will be read out as a video image by the illuminating light having passed through the G filter by the horizontally reading-out register 255.

Likewise, also in the case of the IR2 filter, the unnecessary electric charge by the illuminating light having passed through the B filter and IR1 filter will be read out and will be absorbed by the electric charge absorbing drain 256. On the other hand, the light receiving part 257 will accumulate the signal electric charge by IR2 since just after the unnecessary electric charge is read out and will read out and transfer the electric charge the same as in the case of the above mentioned G filter and a video image a by IR2 will be read out in the register 255.

The case of the UV1 filter is also the same.

Thus, the video signal corresponding to the illuminating light having passed through the respective filters B, IR2 and UV1 and read out in time series will be processed the same as in the sixth embodiment and will be output as a quasi-colorized video signal.

In case a combination of other filters is selected, the driving pattern of the driver circuit 25 will be varied with the switching circuit 223 and a vide signal will be output with any combination.

According to this embodiment, as no shutter part is on the front surface of the solid stat imaging device and the device itself has the function of a shutter, the tip part 189 of the electronic endoscope can be made small. Also, as there is no such mechanical movable part a in the seventh embodiment, the size can be made small and the reliability can be improved.

FIG. 32 shows the ninth embodiment of the present invention.

In this embodiment, the imaging apparatus of the eighth embodiment is applied to an externally fitted television camera fitted to the eyepiece part of a filter scope.

A fiber scope 260 is provided with an elongated, for example, flexible insertable part and a thick operating part 263 connected to this insertable part 262 at the rear end. A flexible light guide cable 264 is extended sidewise from the rear end part of the above mentioned operating part 263. The above mentioned operating part 263 is provided at the rear end with an eyepiece part 265.

The light guide 194 is inserted through the above mentioned insertable part 262 and is arranged on the tip surface in a tip part 266 of an insertable part 262 so as to be able to emit an illuminating light from this tip part 266. The above mentioned light guide 194 is inserted on the entrance end side through the above mentioned light guide cable 264, is connected to a connector not illustrated provided in the tip part of this light guide cable 264 and is connected to the control apparatus 186 through this connector so that the light emitted from the lamp 201 within this control apparatus 186 may enter it.

The above mentioned tip part 266 is provided also with a objective lens system 267 and the tip surface of an image guide 268 is arranged in the image forming position of this objective lens system 267. This image guide 268 is inserted through the above mentioned insertable part 262 and is extended to the above mentioned eyepiece part 265. The object image formed by the above mentioned objective lens system will be led to the eyepiece part 265 by the above mentioned image guide 268 and will be observed from this eyepiece part 265.

An externally fitted television camera 270 can be removably fitted to the above mentioned eyepiece part 265 and is provided with an image forming lens 271 forming an image of the light from the above mentioned eyepiece part 265 and electronic shutter fitted CCD 250 arranged in the image forming position of this image forming lens 271. The same as in the eighth embodiment, this electronic shutter fitted CCD 250 is driven by the driver circuit 258 within the control apparatus 186 and the signal read out will be input into the pre-amplifier 212 and processed the same as in the eighth embodiment.

The other formations, operations and effects are the same as in the eighth embodiment.

By the way, in this embodiment, the externally fitted television camera 270 fitted to the eyepiece part 265 of the fiber scope 260 is provided with the electronic shutter fitted CCD 250 as in the eighth embodiment but may be provided with the liquid crystal shutter 197 as in the sixth embodiment or with the shutter 240 using a piezoelectric device as in the seventh embodiment.

FIGS. 33 to 38 show the tenth embodiment of the present invention.

In this embodiment, an emitted light delicately different in the color and present in a red body wall, for example, within the stomach can be detected by separately radiating a red color light different in the wavelength range.

As shown in FIG. 33, such light source 325 emitting a light of a wide band of wavelengths including a visible range and ranging from an ultraviolet range to an infrared range as, for example, a general hologen or xenon lamp is provided within a video processor 306 forming an electronic endoscope apparatus 300. A condenser lens 326, a rotary filter 328 rotated and driven by a driving part 327 and a rotary shielding plate 314 as a light intercepting means rotated and driven by a driving part 313 are arranged forward of this light source 325. The light emitted form the above mentioned light source 325 will pass through the condenser lens 326, will enter the above mentioned rotary filter 328, will be separated into respective wavelength bands and then will pass through the rotary shielding plate 314.

Figure 38:
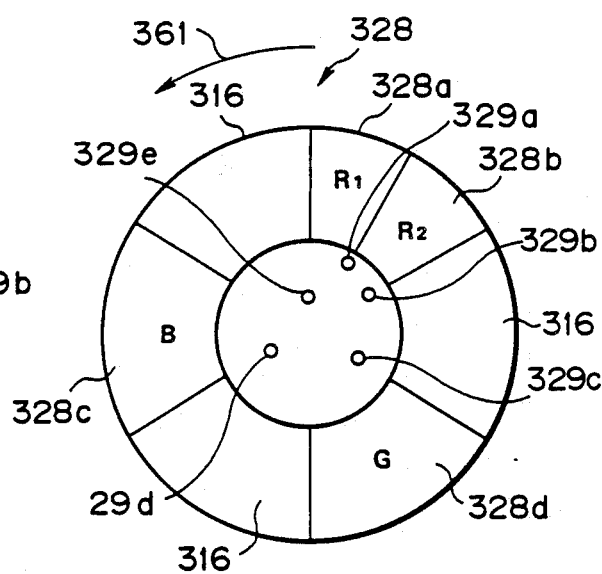

The above mentioned rotary filter 328 is formed as shown in FIG. 38.

Figure 36:
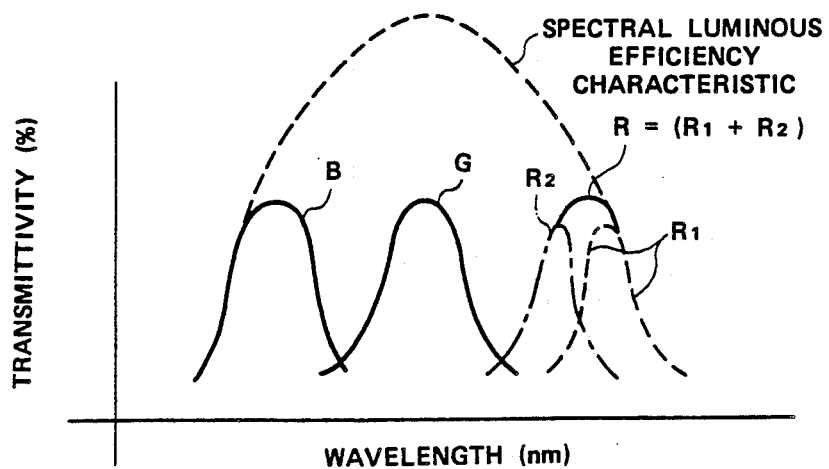

That is to say, the rotary filter 328 is divided into six equal parts, of the six divided parts is further divided into equal parts. These two divided parts are provided respectively with filters 328a and 328b transmitting respectively a first red color light R1 and second red color light R2 having such spectral transmitting characteristics as are shown in FIG. 36. The remaining five parts are provided with shielding parts 316 shielding the light adjacently to the filters 328a and 328b, with a filter 328c transmitting a blue color light B and filter 328d transmitting a green color light G having such spectral transmitting characteristics as are shown in FIG. 36 adjacently to these light intercepting parts 316 and with a light intercepting part 316 shielding the light between the filters 328c and 328d.

As shown in FIG. 36, when the first red color light R1 and second red color light R2 are synthesized, an ordinary red color light R will be made and when these red color light R, green color light G and blue color light B are synthesized, such spectral transmittivity as becomes a specific visual sensitivity characteristic will be made.

The respective filters 328a to 328d of the above mentioned rotary filter 328 are provided on the inner peripheral sides with rotation angle reading marks 329a to 329e for sensing which filter is in the light path of five concentric circles of different radii and forward in the rotating direction of the respective filters 328a to 328d. Also, as shown in FIG. 33, a sensor 331 reading these rotation angle reading marks 329a to 329e is provided as opposed to the above mentioned rotation angle reading marks 329a to 329e.

By the way, the above mentioned rotation angle reading marks 329a ton 329e a may be formed as through holes or parts different in the reflection factor from other parts. The above mentioned sensor 331 may be an optical sensor having a light emitting device and light receiving device arranged as holding the above mentioned rotary filter 328 or on the same side of the rotary filter 328. The above mentioned rotation angle reading marks 329a to 329e may be formed of a magnetic material and the above mentioned sensor 331 may be such magnetic sensor as a hall device. The phase of the rotary filter 328, that is, which filter is in the light path is sensed by the above mentioned sensor 331. This phase information will be input into the above mentioned timing controlling circuit 330.

By the way, in FIG. 38, the arrow 361 indicates the rotating direction of the rotary filter 28.

The above mentioned driving part 327 consists, for example, of a driving motor and motor driver and is controlled in the rotation by the above mentioned timing controlling circuit 330.

Figure 37:
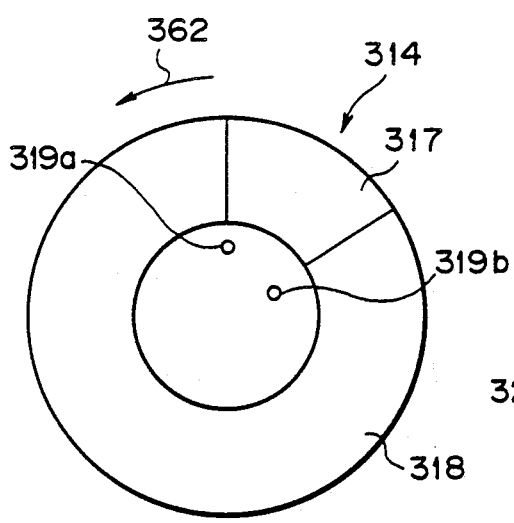

In FIG. 37, the above mentioned rotary shielding plate 314 is of the same outside diameter dimension as of the rotary filter and has in the peripheral direction a concentric circular through filter 318 not limiting the wavelength band of the transmitted light. The light intercepting part 317 is provided in a part of this through filter 318 and is of the same shape as of the light intercepting part 316 provided in the above mentioned rotary filter 328. This light intercepting part 317 is provided on the inner peripheral side with rotation angle reading marks 319a and 319b respectively on two concentric circles of different radii to detect the position of the light intercepting part 317. As shown in FIG. 33, a sensor 322 reading these rotation angle reading marks 319a and 319b is provided as opposed to the rotation angle reading marks 319a and 319b.

By the way, the above mentioned rotation angle reading marks 319a and 319b may be formed as through holes or parts different in the reflection factor from other parts. The above mentioned sensor 322 may optical sensor having a light emitting device and light receiving device arranged as holding the above mentioned rotary shielding plate 314 or on the same side of the rotary shielding plate 314 or the above mentioned rotation angle reading marks 319a and 319b may be formed of a magnetic material and the above mentioned sensor 322 may be such magnetic sensor as a hall device. Whether the light intercepting part 317 is in the light path is sensed by the above mentioned sensor 322. This phase information will be input into the above mentioned timing controlling circuit 330.

By the way, in FIG. 37, the arrow 362 indicates the rotating direction of the rotary shielding plate 314.

The above mentioned driving part 313 consists, for example, of a driving motor and motor driver and is controlled in the rotation by the above mentioned controlling circuit 330.

In this embodiment, the above mentioned video processor 306 is provided, for example, on the operating panel with a setting switch 360 designating the combination of illuminating lights to the above mentioned timing controlling circuit 330. As shown in FIG. 35, this setting switch 360 has a push button switch 360a for the illumination with the respective color lights of B, G and R, a push button switch 360b for the illumination with the respective illuminating lights of B, G and R1 and a push button switch 360c for the illumination with the respective illuminating lights of B, G and R2 so that, when any button among these push button switches 360a to 360c is pushed, the combination of any illuminating lights will be able to be selected. The above mentioned timing controlling circuit 330 controls the rotation phases of the rotary filter 328 and rotary shielding plate 314 with the phase information obtained by reading the rotation angle reading marks 329a to 329e with the sensor 331, the phase information obtained by reading the rotation angle reading marks 319a and 319b provided in the above mentioned rotary shielding plate 314 with the sensor 322 and the information of the combination of the illuminating lights selected by the above mentioned setting switch 360.

The illuminating light having passed through the above mentioned rotary filter 328 and rotary shielding plate 314 will be condensed by a condenser lens 333 and will enter a light guide 335 inserted through a universal cord 304 and insertable part 302 of an electronic endoscope 301 connected through a connector 305. This illuminating light will be led to a tip part 309 through the light guide 335, will be emitted from the tip surface of this light guide and will be projected through a light distributing lens 336 provided in the tip part 309 toward such object to be imaged as a disease part 323 within a body cavity 321 as shown, for example, in FIG. 33.

The above mentioned tip part 309 is provided with an objective lens system 341. A solid state imaging device 342 as an imaging mean is arranged in the image forming position of this objective lens system 341 and has a sensitivity in a wide wavelength range from a visible range to an infrared range.

A driver 343 controlled by the timing controlling circuit 330 is provided within the above mentioned video processor 306 so that a driving signal from this driver 343 will be fed to the above mentioned solid state imaging device 342 through a signal line 344a inserted through the above mentioned universal cord 304 and insertable part 302 and this solid state imaging device 342 will be driven. A signal will be read in time series out of this solid state imaging device 342 as synchronized with the switching of the illuminating light and will be input into pre-processing circuit 345 provided within the above mentioned video processor 306 through a signal line 344b inserted through the above mentioned insertable part 302 and universal cord 304. In this pre-processing circuit 345, a video signal will be extracted, for example, by a sample holding circuit and γ will be corrected by a γ correcting circuit. The output signal of this pre-processing circuit 345 will be converted to a digital signal by an A/D converter 346, will be switched as synchronized with a frame sequential illumination by a multiplexer 347 controlled to be switched by the above mentioned timing controlling circuit 330 and will be memorized in frame memories 348, 349 and 350 corresponding to the respective colors of red, green and blue in turn. The outputs of these frame memories 348, 349 and 350 will be simultaneously read out at a speed matching such displaying apparatus a the monitor 7 and will be converted to analog signals respectively by D/A converters 351, 352 and 353 to produce R, G and B signals. Thus, in this embodiment, the respective colors of R, G and B will be freely allotted respectively to the output signals of the solid state imaging device 342 corresponding to three modes selected by the above mentioned setting switch 360 to produce R, G and B color signals.

These R, G and B color signals will be output from R, G and B color exit ends 355 and will be at the same time input into an NTSC encoder 356 and will be converted to an NTSC signal which will be output from an NTSC output end 357. A color monitor 307 corresponding to three primary colors can be connected to the above mentioned R, G and B output ends 355. On the other hand, a color monitor 307 into which a video signal of an NTSC system is to be input can be connected to the above mentioned NTSC output end 357. The monitor 307 of either system can be used. An object image will be color-displayed in this monitor 307.

By the way, a terminal through which a synchronous signal SYNC from the timing controlling circuit 330 can be output is also provided along with the above mentioned R, G and B output ends 355 so that the above mentioned synchronous signal SYNC together with the above mentioned R, G and B color signals ma be input into the color monitor 307 corresponding to the above mentioned three primary colors.

The operation of the embodiment of the above formation shall be explained in the following.

First of all, in the case of obtaining a color picture image faithful to an ordinary color reproduction, the push button switch 360a corresponding to the respective illuminating lights of R, G and B is pushed with the setting switch 360. The timing controlling circuit 330 will control the driving parts 313 and 327 so that the rotation angle reading marks 329b and 319a may be rotated in the same phase by the phase information obtained by reading the rotation angle reading marks 319a, 319b and 329a to 329e with the sensors 322 and 331 and the information of the combination of the illuminating lights selected by the above mentioned setting switch 360 and will rotate the rotary filter 328 and rotary shielding plate 314 at the same speed in such phase as is mentioned above. The color lights of (R1 +R2), G and B having passed through these respective filters 328a to 328d will be radiated to an object in time series. The reflected lights by the object corresponding to the respective illuminating lights of (R1 +R2), G and B will be photoelectrically converted by the solid state imaging device 342 and will be read out in time series as synchronized with the switching of the illuminating lights.

The video signals corresponding to the respective illuminating lights (R1 +R2), G and B, read out of the above mentioned solid state imaging device 342 and having passed through the pre-processing circuit 345 will be memorized respectively in the frame memories 348, 349 and 350 corresponding respectively to (R1 +R2), G and B. These frame memories 348, 349 and 350 will be read out to produce R, G and B color signals and an NTSC signal and the object image will be color-displayed in the color monitors 307.

On the other hand, in case a mode different from the ordinary illumination is selected, it will be as follows.

For example, when the push button switch 360b corresponding to respective color lights of R1, G and B is pushed with the setting switch 360, the timing controlling circuit 330 will control the driving parts 313 and 327 so that the rotation angle reading marks 329a and 319a may be rotated in the same phase by the phase information obtained by reading the rotation angle reading marks 319a, 319b and 329a to 329e with the sensors 322 and 331 and the information of the combination of the illuminating lights selected by the above mentioned setting switch 360 and will rotate the rotary filter 328 and rotary shielding plate 314 at the same speed in such phase as is mentioned above. The color lights of R1, G and B having passed through these respective filters 328a, 328c and 328d will be radiated to an object in time series. The reflected lights by the object corresponding to the respective illuminating lights R1, G and B will be photoelectrically converted by the solid state imaging device 342 and will be read out in time series as synchronized with the switching of the illuminating lights.

The video signals corresponding to the respective illuminating lights R1, G and B will be memorized respectively in the frame memories 348, 349 and 350 corresponding respectively to R, G and B. The other operations are the same as in the above described case.

Therefore, the video signal by the illuminating light R1 will be handled as ordinary red and the object will be displayed in quasi colors.

In case another mode different from the ordinary illumination is selected, it will be as follow.

When the push button switch 360c corresponding to the respective color lights of R2, G and B is pushed with the setting switch 360, the timing controlling circuit 330 will control the driving parts 313 and 327 so that the rotation angle reading marks 329a and 319b may be rotated in the same phase by the phase information obtained by reading the rotation angle reading marks 319a, 319b and 329a to 329e with the sensors 322 and 331 and the information of the combination of the illuminating lights selected by the above mentioned setting switch 360 and will rotate the rotary filter 328 and rotary shielding plate 314 at the same speed in such phase as is mentioned above.

Figure 34:
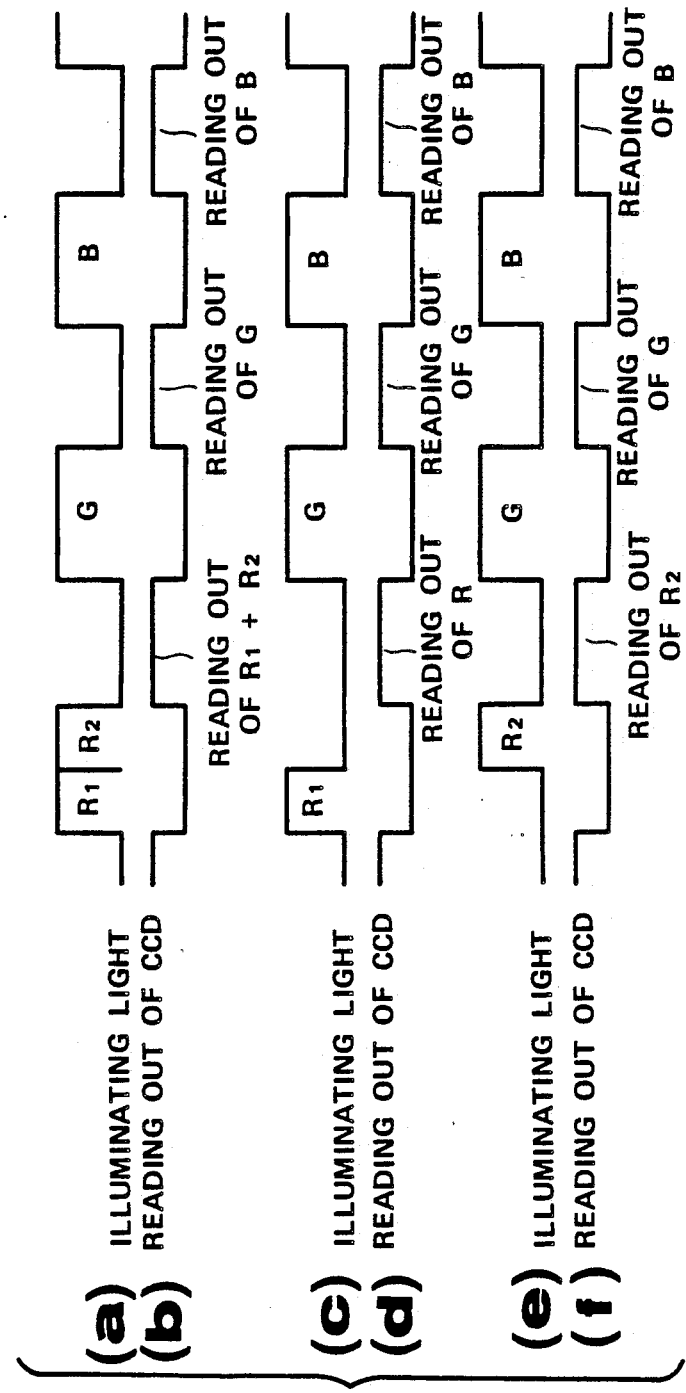

By the way, in case the mode of the ordinary illumination is selected by the push button switch 360a, the video signal will be read out of the solid state imaging device 342 after the illuminating light passes through the filters 328a and 328b and the color light of (R1 +R2) is radiated as shown in FIGS. 34 (a) and (b).

In case the mode different from the ordinary illumination is selected by the push button switch 360b, R1 will be read out after the color light of %2 having passed through the filter 328b is intercepted by the light intercepting part 317 as in FIGS. 34 (c) and (d).

Further, in case another mode different from the ordinary illumination is selected by the push button switch 360c, as in FIGS. 34 (e) and (f), the color light of R2 having passed through the filter 328b will be radiated after the color light of R1 having passed through the filter 328a is intercepted by the light intercepting part 317 and then R2 will be read out.

Thus, according to this embodiment, a red emission delicately different in the color and present in a red body wall, for example, within the stomach can be detected by separately radiating red lights R1 and R2.

Further, the aperture areas of the filters 328a to 328d are made so large that the illuminating light fed to the electronic endoscope 301 can be effectively used and the light amount can be taken to be large.

By the way, not only the rotary shielding plate 314 but also a shutter may be provided and may be opened and closed as synchronized with the rotation of the rotary filter 328. Not only the mechanical shutter but also, for example, a liquid crystal plate which can electrically control the transmittivity may be used.

Further, in this embodiment, R1, R2 and R1 +R2 are made to correspond to R, G is made to correspond to G and B is made to correspond to B. The invention is not limited to them. The quasi-colorization may be made by whatever correspondence.

Further, instead of manually selecting the illuminating light with the setting switch 360, the illuminating light may be automatically alternately switched so that, for example, the video image by the R, G and B illumination which is a mode good in general color reproduction and the video image by the R1, G and B illumination which is a mode for special light observation may be displayed in two pictures in one monitor 307.

Figure 39:
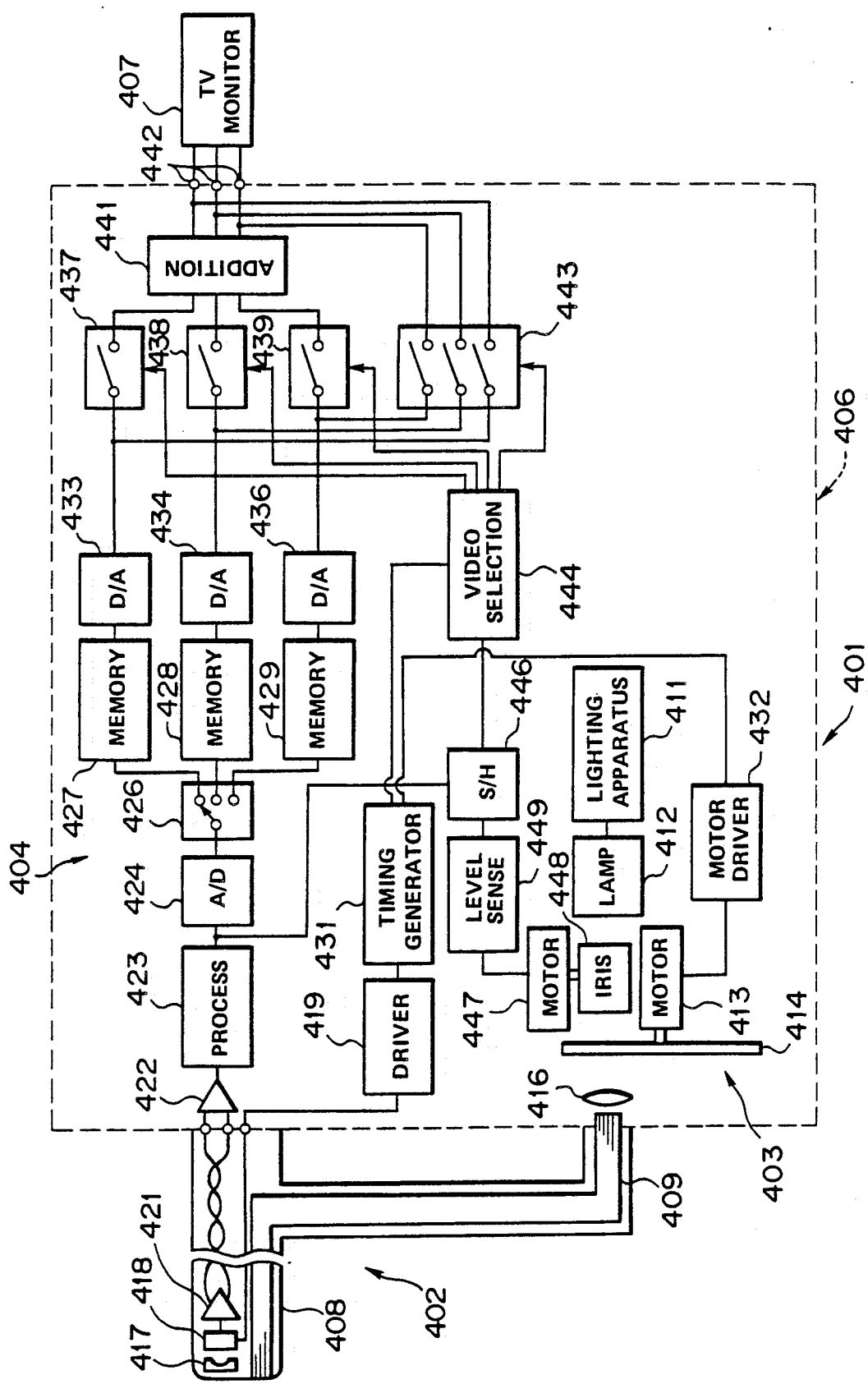
FIG. 39 is a formation explaining view of an endoscope relating to the 11th embodiment of the present invention.

FIG. 39 shows the 11th embodiment of the present invention.

An endoscope apparatus 401 of this embodiment comprises an electronic endoscope 402, an endoscope controlling apparatus 406 to which this electronic endoscope 402 is connected on the rear end side and which contains a light source part 403 and signal processing part 404 and a TV monitor 407 into which video signals output from this (endoscope) controlling apparatus 406 are input and which displays endoscope picture images.

The above mentioned electronic endoscope 402 has an elongated insertable part 408 to be able to be inserted into a living body. A light guide 409 transmitting an illuminating light and emitting it from the tip surface is inserted through this insertable part a body inside illuminating light is fed from a light source part 403 to the entrance end surface on the base side of this light guide 409.

The light source part 403 feeds an electric power to a lamp 412 from a lighting apparatus 411 to make this lamp 412 emit a light. The white color light emitted from this lamp 412 will be made color sequential illuminating lights of red, green and blue through a rotary filter 414 as a spectral means rotated and driven by a sync motor 413, then will be condensed by a condenser lens 416 and will be radiated to a light guide 409 on the entrance end surface. By the way, the above mentioned rotary filter 419 consists of a red transmitting filter, green transmitting filter and blue transmitting filter, fitted respectively in three fan-like apertures made in the peripheral direction of a light intercepting disk. The light reflected by a living body illuminated by the above mentioned body inside illumination will be made to form an image on the imaging surface of a charge coupled device (mentioned as a CCD) 418 as a solid state imaging device by the objective lens 417. This CCD 418 will photoelectrically convert the optical image formed on the imaging surface. When a CCD driving signal from a CCD driver 419 is applied, the CCD will output a photoelectrically converted video signal. The signal output from this CCD 418 will be amplified by a preamplifier 421, will be output as a differential video signal to a differential amplifier 422 provided within the control apparatus 406 and will be further differentially amplified by this differential amplifier 422.

The video signal amplified by the above mentioned differential amplifier 422 will be processed to have the white balance and $\gamma$ corrected in a processing circuit 423 and will be input into an A/D converter 424 digitalizing the analog video signal. The digitalized video signals will be read out in time series by a selector 426 and will be divided and recorded in a memory 427 recording the picture image obtained by the illuminating light of blue (B), a memory 428 recording the picture image obtained by the illuminating light of blue (B) and a memory 429 recording the picture image obtained by the illuminating light of red (R).

A control signal determining the timing of outputting a CCD driving signal out of a timing generator 431 generating a timing signal of the entire system will be applied to the above mentioned CCD driver 419. This timing generator 431 will apply a control signal determining the motor 413 rotating timing to the motor driver 432 applying a motor driving signal to the above mentioned motor 413. Further, the timing generator 431 will apply a control signal to the above mentioned selector 426 so that the picture images obtained by the respective illuminating lights corresponding to the respective memories 427, 428 and 429 may be recorded.

The respective picture images recorded in the above mentioned memories 427 428 and 429 will output three primary color signals of R, G and B to the TV monitor 407 as a displaying means from an output end through switching circuits 437, 438 and 439 switching on and off the outputs of the respective color signals of red (R), green (G) and blue (B) made analogs respectively by D/A converters 433, 434 and 436 and an adding circuit 441 adding the respective signals to be made monochromatic signals.

By the way, the respective color signals from the D/A converters 433, 434 and 436 will be branched and will be led to the above mentioned output ends 422 through a switching circuit 443 simultaneously switching on and off the outputs of the respective color signals.

The above mentioned switching circuit 437, 438 and 439 and a switching circuit 443 will be controlled by a video image selecting circuit 444 as a selecting means selecting the outputs of the picture images of R, G and B, the monochromatic picture image of the combination of them and further the color picture images by R, G and B. In this video image selecting circuit 444, a synchronous signal will be applied from the timing generator 431, a control signal will be output to a sample holding circuit 446 and the video signal output from the processing circuit 423 and corresponding to the output selected picture image will be sampled and held.

The video signal sample-held in the above mentioned sample holding circuit 446 will have the signal level detected by a level sensing circuit 449 as an exposure detecting means and will be adjusted by an iris 448 driven by a motor 447 so that the light amount emitted from the lamp 412 may be proper.

Now, the operation of the endoscope apparatus formed as mentioned above is as follows.

A light will be emitted from the lamp 412 of the light source part 403 by applying an electric power from the lighting apparatus 411, will be controlled by the iris 448 within the light path to be of the optimum exposure level, then will be color-separated in time series by the disc-like rotary filter 414 having transmitting ranges in the respective wavelength ranges of R, G and B, will be condensed by the condenser lens 416 and will enter the light guide 409 on the entrance end surface. The respective lights of R, G and B will be transmitted through the light guide 409 and will be radiated from the tip part of the insertable part 408 of the endoscope 402 to a part to be observed within a body cavity. The optical image of the observed part will be formed on the imaging surface of the CCD 418 by the objective lens 417, will be photoelectrically converted to a video signal, will be read out of the CCD 418 by a CCD driving signal applied from the CCD driver 419 will be amplified by the preamplifier 421 and differential amplifier 422, will be input into the processing circuit 423 and will be processed to be a video signal in the processing circuit 423. The video signal will be digitalized by the A/D converter 424, will be color-separated in time series by the selector 426 switched as synchronized with reading out. These separated signals will be recorded in the memories 427, 428 and 429. The signals recorded in these respective memories 427, 428 and 429 will be made analogs respectively by the D/A converters 433, 434 and 436 and will be input into the switching circuits 437, 438, 439 and 443 which will be operated to be on and off by the video signal selecting circuit 444. In case the switching circuits 437, 438 and 439 are switched on by the video signal selecting circuit 444, the picture images of the respective wavelength ranges of R, G and B will be synthesized by the adding circuit 441 and then will be output as a monochromatic signal in the TV monitor 407 to display a monochromatic image. In case the switching circuit 443 is switched on, R, G and B signals will be directly output in the TV monitor 407 to display a color picture image. Further, in case any one of the switching circuits 437, 438 and 439 is switched on, any one of R, G and B picture images will be able to be displayed in the TV monitor 407.

On the other hand, among the video signals output from the processing circuit 423, the video signal corresponding to each or a combination of the R, G and B picture images selected by the video image selecting circuit 444 will have the exposure level detected by the sample holding circuit 446 and level sensing circuit 449 and will have the exposure controlled by driving the iris 448 with the motor 447.

By the formation and operation of this embodiment, among the picture images peculiar to the respective wavelengths by the difference in the penetrating degree, reflection factor and absorbing rate of a light in the mucous membrane tissue, a picture image of a proper exposure can be obtained. That is to say, the R picture image is high in the penetrating degree and therefore, through it is not proper form such minute observation as of concavo-convexes on the surface, with the R picture image, the vein running state, tumor penetrating range and blood filled state in the part below the mucous membrane which can not be observed with a light on the short wavelength side can be observed. The B picture image on the short wavelength side is low in the penetrating degree of a light and therefore does not include the information below the mucous membrane and, with it, the concavo-convexes on the surface and the veins near the extreme surface of the membrane can be easily observed.

As in the above, the respective wavelength ranges have features in the living body observation. Therefore, when a color picture image near the ordinary observation with a naked eye and picture images of specific wavelengths having respective features are displayed and further the exposure level optimum to the switched and displayed picture image is obtained, the disease will be able be easily observed and a high degree diagnosis will be possible.

By the way, instead of inputting the color signals of R, G and B into the TV monitor 407, the monochromatic and color signals may be replaced with such composite video signal as of an NTSC system. The level sensing circuit 449 may detect the signal level just before the signal is input into the TV monitor 407.

Figure 40:
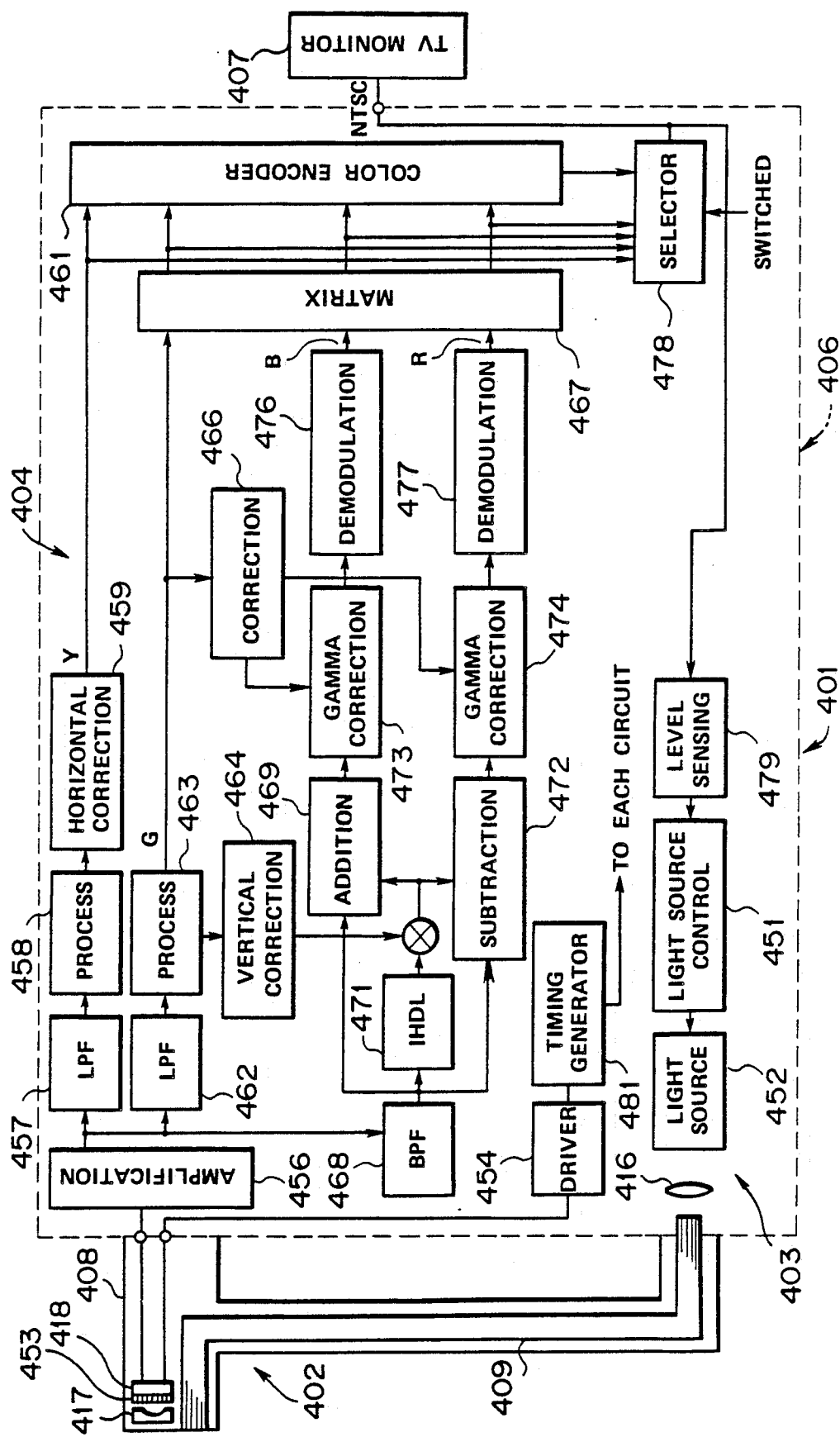
FIG. 40 is a formation explaining view of an endoscope relating to the 12th embodiment of the present invention.

FIG. 40 shows the 12th embodiment of the present invention.

An endoscope apparatus 401 of this embodiment comprises an electronic endoscope 402, an endoscope controlling apparatus 406 to which this electronic endoscope 402 is connected on the rear end side and which contains a light source part 403 and signal processing part 404 and a TV monitor 407 into which video signals output from this (endoscope) controlling apparatus 406 are input and which displays endoscope picture images.

The above mentioned electronic endoscope 402 has an elongated insertable part 408 to be able to be inserted into a living body. A light guide 409 transmitting an illuminating light and emitting it from the tip surface is inserted through this insertable part. A body inside illuminating light is fed from a light source part 403 to the entrance end surface on the base side of this light guide 409.

This light source part 403 feeds an electric power to a light source 452 from a light source controlling apparatus 451 to make the light source 452 emit a white color light.

An observed image within a living body illuminated by the above mentioned body inside illuminating light will be formed on the imaging surface of a CCD 418 provided with a mosaic-like color separating filter 453 color-separating an optical image formed by an objective lens 417. This formed observed image will be photoelectrically converted and will be output from the CCD 418 when a CCD driving signal from a CCD driver 454 is applied. The CCD driver 454 will generate a CCD driving signal by a synchronous signal applied from a timing generator 481 generating and synchronizing the timing of the entire system.

The signal output from the above mentioned CCD 418 will be amplified by an amplifier 456 and will be output to low pass filters 457 and 462 and a band pass filter 468. This low pass filter 457 will pass the signal of a luminance component of the input video signal and will output it to a processing circuit 458 making the signal of the CCD 418 an observable video signal. Further, this video signal will pass through a horizontal correcting circuit 459 correcting the rise of the signal in the horizontal direction and will be output to a color encoder 461. The above mentioned low pass filter 462 will pass the color signal of G among the picture image signals of CCD 418. The color signal having passed through this low pass filter 462 will be processed by this processing circuit 462 so as to be an observable video signal. The output signal of this processing circuit 463 will be output to a vertical correcting circuit 464 correcting the rise in the vertical direction, a correcting circuit 466 generating a correcting signal for correcting γ and a matrix circuit 467. Further, a band pass filter 468 will separate the color signal component modulated by the color separating filter 453 and will output this color signal component to an adding circuit 469, 1H delay circuit 471 and subtracting circuit 472. In the above mentioned 1H delay circuit 471, the signal will be delayed by 1H period. This delayed signal will be output to the above mentioned adding circuit 469 and a subtracting circuit 472 to be respectively added and subtracted.

The outputs of the adding circuit 469 and subtracting circuit 472 will have γ corrected respectively by γ correcting circuits 473 and 474 controlled by the above mentioned correcting circuit 466, then will be demodulated by respective demodulating circuits 476 and 477, will have the color signal have a measurably accurate color reproducibility in the above mentioned matrix circuit 467 and will be input into the above mentioned color encoder 461. In this color encoder 461, an NTSC system composite video signal will be produced from the luminance signal and respective color signals and will be output to a selector circuit 478. Not only the NTSC composite video signal but also the respective color signals will be input into this selector circuit 478 so that each or a combination of the respective color signals and the NTSC composite video signal may be switched. The output of the selector circuit 478 will be output to a TV monitor 407 and a level sensing circuit 479 detecting the signal level and outputting a control signal to a light source controlling circuit 451.

Now, the operation of the endoscope apparatus 401 formed as mentioned above is as follows.

The illuminating light emitted from the light source 452 will be condensed by the condenser lens 416 and will be transmitted through the light guide 409 to illuminate a part to be observed. Th light reflected from the illuminated living body mucous membrane will pass through the color separating filter 453 and will form an image on the imaging surface of the CCD 418 by the objective lens 417 provided in the tip part of the endoscope. The above mentioned color separating filter 453 will color-separate the reflected light into colors of wavelength ranges different in the activity of observing the living body mucous membrane.

In the above mentioned CCD 418, the formed observed image will be photoelectrically converted to a picture image signal, will be read out when a CCD driving signal from the CCD driver 454 is applied, will be amplified by the amplifier 456 and will be output to the low pass filters 457 and 462 and band pass filter 468. A luminance component in the picture image signal will pass through the low pass filter 457 and will be input into the color encoder 461 as a video signal showing the luminance component through the processing circuit 458 and horizontal correcting circuit 459. The above mentioned low pass filter 462 will input the video signal as a video signal of G into the matrix circuit 467 through the processing circuit 463. Further, one side of the output signal of the band pass filter 468 will be output to the matrix circuit 467 as a B signal having the signal through the 1H delay circuit 471 added by the adding circuit 467 and passed through the γ correcting circuit 473 and demodulating circuit 467. The other side of the output signal will be output to the matrix circuit 467 as an R signal having the signal through the 1H delay circuit subtracted by the subtracting circuit 472 and passed through the γ correcting circuit 471 and demodulating circuit 477. The respective color signals will be adjusted to be measurably accurately color reproducible, then will be converted to an NTSC video signal by the color encoder 464 and will be input into the selector circuit 478.

In the above mentioned selector circuit 478, a video signal of each or a combination of the color signals of the respective wavelength ranges output from the matrix circuit 467, a video signal of a monochromatic signal or a varied color signal of two colors and a video signal of general colors will be selected and output by a switching signal. The exposure level will be detected with the level sensing circuit 479 so that the color balance may not vary in case the output video signal is a video signal of colors and so that the exposure level may be most adapted to the observation in case a single color or a combination of two colors is output and then the light source 452 will be controlled by the light source controlling circuit 451.

By the above formation, the same effect as of the 12th embodiment can be realized with the electronic endoscope using no rotary filter and the diagnosing activity can be improved by the characteristic description of respective wavelength ranges together with the diagnosis by a general color picture image.

In both 11th and 12th embodiments, not only the light in the visible light range but also the lights in the ultraviolet light and infrared light ranges may be used.

In both 11th and 12th embodiments, if the distribution of hemoglobin in the mucous membrane or the like is observed in the wavelength ranges of G and B, the R component will not be included and therefore the observation will be possible at a contrast higher than in the general color picture image.

If a light on the short wavelength side of and ultraviolet light or visible light is projected out of the light source to excite a substance inherent to a living body or a fluorescent substance and the wavelength range of the emitted fluorescence is observed, the fluorescence will be able to be observed at a high S/N ratio without masking the exciting light source.

As explained above, according to the present invention, a visible information can be obtained by selecting the optimum wavelength range in response to an object to be observed and the respective parts of the observed object difficult to discriminate with a picture image of the general visible range can be easily observed.

What is claimed is:

1. An endoscope apparatus comprising:
   a light source for emitting a light illuminating an object to be imaged;
   an endoscope body having an elongated insertable portion with an observing widow and illuminating window in the tip portion of said insertable portion, a light transmitter for transmitting said light of said light source and for emitting said light to an object from said illuminating window, and an image forming optical system for receiving returning light based on illuminating light having different wavelength ranges from said object entering through said observing window and forming an object image;

an imaging means for imaging said object image formed by said image forming optical system and for outputting said object image as an electric signal;

a signal processing means for receiving and processing said electric signal of said imaging means based on said illuminating light having different wavelength ranges, and for outputting a picture image signal, wherein said picture image signal outputted from said signal processing means can be directly displayed as a picture image of an object;

a wavelength range separating means for separating said object image into a plurality of wavelength ranges;

a selecting means for selecting a wavelength range clearly representing a state of said object from among a plurality of said separated wavelength ranges; and an operating means operably coupled to said signal processing means for receiving and processing said picture image signal which can be directly displayed as a picture image of an object, wherein said picture image signal is processed by said operating means based on said wavelength range selected by said selecting means and for outputting a signal which when displayed clearly represents said state of said object.

2. An endoscope apparatus according to claim 1 wherein said imaging means is a solid state imaging device.

3. An endoscope apparatus according to claim 2 wherein said solid state imaging device is arranged in the image forming position of said image forming optical system within the tip part of the insertable part of said endoscope body.

4. An endoscope apparatus according to claim 1 wherein said endoscope body is further provided with an eyepiece part provided on the rear end side of said insertable part and an image transmitting means transmitting the object image formed by said image forming optical system to said eyepiece part and said imaging means is a television camera having a solid state imaging device removably fitted to said eyepiece part.

5. An endoscope apparatus according to claim 4, wherein said wavelength range separating means is a rotary filter in which wavelength range separating filters separating different wavelength ranges are provided in the peripheral direction.

6. An endoscope apparatus according to claim 4 wherein said solid state imaging device provided in the television camera is an electronic shutter fitted said solid state imaging device which is also a selecting means, having an electric charge absorbing drain absorbing an unnecessary electric charge, reading out only an electric charge of a light by a wavelength range adapted to the object observation and transferring the unnecessary electric charge from said electric charge absorbing drain.

7. An endoscope apparatus according to claim 3, wherein said wavelength range separating means is a rotary filter in which wavelength range separating filters separating different wavelength ranges are provided in the peripheral direction.

8. An endoscope apparatus according to claim 3, wherein said wavelength range separating means is a rotary filter having a wavelength range separating filter group for separating different wavelength ranges and further having a plurality of said wavelength range concentrically arranged in said rotary filter for separating filter groups.

9. An endoscope apparatus according to claim 8 wherein said wavelength range separating filter group is formed of a wavelength range separating filter transmitting a wavelength range in which the light absorbing degree of a blood varies with the variation of the oxygen saturation degree of hemoglobin and a wavelength range separating filter transmitting a wavelength range in which the light absorbing degree of a blood varies little with the variation of the oxygen saturation degree of hemoglobin.

10. An endoscope apparatus according to claim 8 wherein said wavelength separating filter group is formed of wavelength range separating filters transmitting three wavelength ranges to obtain a general color picture image.

11. An endoscope apparatus according to claim 3 wherein said wavelength separating means has a plurality of kinds of rotary filters provided in the peripheral direction with wavelength range separating filters sep rating different wavelength ranges.

12. An endoscope apparatus according to claim 11, wherein at least one of said rotary filters includes a wavelength range separating filter which is formed of a wavelength range separating filter for transmitting the wavelength range in which the light absorbing degree of a blood varies with the variation of the oxygen saturation degree of hemoglobin, and a wavelength range separating filter for transmitting another wavelength range which is near said wavelength range and in which the light absorbing degree of a blood varies little with the variation of the oxygen saturation degree of hemoglobin in order to select a most suitable wavelength range in response to said object to be imaged to thereby provide a picture image showing variations of oxygen saturation degree and amount of hemoglobin and to thereby switch and observe blood flow at different wavelength ranges.

13. An endoscope apparatus according to claim 11 wherein said wavelength range separating filter provided in at least one rotary filter is formed of wavelength range separating filters transmitting three wavelength ranges to obtain a general color picture image.

14. An endoscope apparatus according to claim 3 wherein said wavelength range separating means is a filter in which a main wavelength of a band pass characteristic of a narrow band continuously varies with the position in the peripheral direction and is a rotated and driven linear interfering filter.

15. An endoscope apparatus according to claim 14 wherein said linear interfering filter comprises wavelength range separating filters transmitting at least three wavelength ranges for obtaining a general color picture image and a wavelength range in which the light absorbing degree of a blood varies with the variation of the oxygen saturation degree of hemoglobin and a wavelength range separating filter transmitting a wavelength range which is near said wavelength range and in which the light absorbing degree of a blood varies little with the variation of the oxygen saturation degree of hemoglobin.

16. An endoscope apparatus according to claim 3 wherein said wavelength range separating means comprises a beam splitter separating the returning light from said object into two directions, an ordinary observation color filter array transmitting one part of the light separated by said beam splitter and a special observation color filter array transmitting the other part of the light.

17. An endoscope apparatus according to claim 16 wherein said ordinary observation color filter array comprised wavelength range separating filters transmitting respectively three wavelength ranges for obtaining a general color picture image.

18. An endoscope apparatus according to claim 16 wherein said special observation color filter array comprises a wavelength range separating filter transmitting a wavelength range in which the light absorbing degree of a blood varies with the variation of the oxygen saturation degree of hemoglobin and a wavelength range separating filter transmitting a wavelength range which is near said wavelength range and in which the light absorbing degree of a blood varies little with the variation of the oxygen saturation degree of hemoglobin.

19. An endoscope apparatus according to claim 7 wherein at least one rotary filter is a rotary filter having wavelength range separating filters separating three primary colors of red (R), green (G) and blue (B) for obtaining a general color picture image.

20. An endoscope apparatus according to claim 7 wherein said rotary filter has wavelength range separating filters separating the respective wavelength ranges of an ultraviolet light, visible light and infrared light into narrower bands.

21. An endoscope apparatus having a wavelength range separating means according to claim 8 wherein said selecting means can select a wavelength range separating filter group by moving said rotary filter in the direction intersecting at right angles with the optical axis of said light source part.

22. An endoscope apparatus having a wavelength range separating means according to claim 11 wherein said selecting means selects a rotary filter having a wavelength range adapted to the object observation from among a plurality of rotary filters and interposed said selected rotary filter in the optical axis.

23. An endoscope apparatus having a wavelength range separating means according to claim 16 wherein said selecting means is a switching switch selecting an output signal from said solid state imaging device to which is pasted an ordinary observation color filter array and an output signal from said solid state imaging device to which is pasted a special observation color filter array.

24. An endoscope apparatus having a wavelength range separating means according to claim 14 wherein said selecting means is a light emitting signal generating circuit transmitting a light emitting signal to said light source part when the part transmitting a wavelength adapted to the object observation is interposed in the optical axis in said linear interfering filter.

25. An endoscope apparatus having a wavelength range separating means according to claim 7 wherein said selecting means is a liquid crystal shutter transmitting the object image only when the wavelength range is adapted to the object observation.

26. An endoscope apparatus according to claim 25 wherein said liquid crystal shutter is provided on the front surface of said solid state imaging device.

27. An endoscope apparatus according to claim 25 wherein said liquid crystal shutter is provided between said light source part and rotary filter.

28. An endoscope apparatus according to claim 25 wherein said liquid crystal shutter is provided between said rotary filter and the entrance end surface of said light transmitter.

29. An endoscope apparatus having a wavelength range separating means according to claim 7 wherein said selecting means comprises a filter having a transmitting part and light intercepting part and arranged on the imaging surface of the solid state imaging device and a piezoelectric oscillator moving said filter to position alternately said transmitting part and light intercepting part on the photosensitive part of said solid state imaging device.

30. An endoscope apparatus having a wavelength range separating means according to claim 7 wherein said solid state imaging device is an electronic shutter fitted solid state imaging device being also a selecting means, having an electric charge absorbing drain absorbing an unnecessary electric charge, reading out only an electric charge by the light of the wavelength range adapted to the object observation and transferring the unnecessary electric charges out of the electric charge absorbing drain.

31. An endoscope apparatus having a wavelength range separating means according to claim 7 wherein said selecting means is a rotary shielding plate having a light transmitting part and light shielding part, rotating synchronously with said rotary filter, transmitting with said light transmitting part the wavelength range having passed through the wavelength range separating filter of said rotary filter and adapted to the object observation and shielding others with said light shielding part.

32. An endoscope apparatus having a wavelength range separating means according to claim 19 wherein said selecting means is a switching switch selecting at least one color signal from the color signals R, G and B processed by said signal processing means.

33. An endoscope apparatus having a wavelength range separating means according to claim 19 wherein said selecting means is a selecting circuit selecting at least one signal from among a luminance signal Y and color signals R, G and B.

34. An endoscope apparatus according to claim 32 or 33 further comprising a light source controlling means adjusting the light amount emitted out of said light source part so that the picture image by the selected signal may be of the optimum exposure level.

35. An endoscope apparatus according to claim 1, wherein said operating means produces a signal representing oxygen saturation degree, amount of blood flow, and amount of hemoglobin.

* * * * *

UNITED STATES PATENT AND TRADEMARK OFFICE
CERTIFICATE OF CORRECTION

PATENT NO. : 5,001,556

DATED : March 19, 1991

INVENTOR(S) : Kazunari NAKAMURA et al

It is certified that error appears in the above-identified patent and that said Letters Patent is hereby corrected as shown below:

On the cover page, Item [30], third line, "62-26838" should read -- 63-26838 --.

On the cover page, Item [30], fourth line, "62-105971" should read -- 63-105971 --.

Signed and Sealed this

Twelfth Day of January, 1993

Attest:

DOUGLAS B. COMER

*Attesting Officer*     Acting Commissioner of Patents and Trademarks